(12) United States Patent
Lam et al.

(10) Patent No.: US 11,045,576 B2
(45) Date of Patent: Jun. 29, 2021

(54) COMPOSITION COMPRISING A POLYMER AND A SWITCH INITIATOR

(71) Applicant: Coloplast A/S, Humlebaek (DK)

(72) Inventors: Peter Kwok Hing Lam, Frederiksberg C (DK); Esben Stroebech, Hoersholm (DK); Kristoffer Hansen, Naerum (DK); Anders Grove Sund, Dyssegaard (DK); Anca Gabriela Bejenariu, Koebenhavn S (DK); Charlotte Juel Fristrup, Virum (DK); Bahar Bingol, Copenhagen OE (DK)

(73) Assignee: Coloplast A/S, Humlebaek (DK)

( * ) Notice: Subject to any disclaimer, the term of this patent is extended or adjusted under 35 U.S.C. 154(b) by 903 days.

(21) Appl. No.: 15/517,519

(22) PCT Filed: Oct. 8, 2015

(86) PCT No.: PCT/DK2015/050305
§ 371 (c)(1),
(2) Date: Apr. 7, 2017

(87) PCT Pub. No.: WO2016/055075
PCT Pub. Date: Apr. 14, 2016

(65) Prior Publication Data
US 2017/0239384 A1 Aug. 24, 2017

(30) Foreign Application Priority Data

Oct. 9, 2014 (DK) .......................... PA 2014 70626
Dec. 9, 2014 (DK) .......................... PA 2014 70770
Feb. 2, 2015 (DK) .......................... PA 2015 70057
Mar. 24, 2015 (DK) .......................... PA 2015 70166
Apr. 10, 2015 (DK) .......................... PA 2015 70210
Apr. 30, 2015 (DK) .......................... PA 2015 70255

(51) Int. Cl.
*A61L 24/00* (2006.01)
*A61F 5/443* (2006.01)
*A61L 24/04* (2006.01)

(52) U.S. Cl.
CPC .......... *A61L 24/0031* (2013.01); *A61F 5/443* (2013.01); *A61L 24/043* (2013.01); *A61L 2400/14* (2013.01)

(58) Field of Classification Search
CPC combination set(s) only.
See application file for complete search history.

(56) References Cited

U.S. PATENT DOCUMENTS

| | | | | |
|---|---|---|---|---|
| 3,612,053 A * | 10/1971 | Pratt | .................... | A61L 28/0011 604/338 |
| 4,831,070 A * | 5/1989 | Mclnally | ................. | A61L 15/58 524/267 |
| 5,087,686 A * | 2/1992 | Ansell | .................... | C08G 18/10 528/49 |
| 6,068,852 A * | 5/2000 | Shah | ....................... | A61F 5/443 424/401 |
| 6,359,100 B1 * | 3/2002 | Hostettler | .............. | C08G 18/12 528/58 |
| 2002/0128614 A1 * | 9/2002 | Cinelli | .................. | A61L 15/585 604/332 |
| 2004/0065232 A1 * | 4/2004 | Lykke | ................... | A61L 15/585 106/680 |
| 2005/0215727 A1 * | 9/2005 | Feldstein | ................. | A61P 17/02 525/326.9 |
| 2006/0228318 A1 * | 10/2006 | Fabo | ....................... | A61L 15/26 424/70.12 |
| 2006/0251890 A1 * | 11/2006 | Lane | ......................... | C09J 7/22 428/343 |
| 2006/0263596 A1 * | 11/2006 | Bamborough | .......... | B32B 27/16 428/354 |
| 2007/0009582 A1 * | 1/2007 | Madsen | ................ | A61L 15/585 424/445 |
| 2007/0231571 A1 * | 10/2007 | Lane | ......................... | C09J 7/38 428/354 |
| 2011/0224593 A1 * | 9/2011 | Tunius | ................... | C09J 133/08 602/54 |
| 2011/0262858 A1 * | 10/2011 | Nair | ..................... | G03G 9/0902 430/110.2 |
| 2012/0022210 A1 * | 1/2012 | Davio | .................... | C07F 9/065 524/588 |
| 2012/0123220 A1 * | 5/2012 | Iyer | ..................... | A61F 13/0223 600/300 |
| 2013/0017246 A1 * | 1/2013 | Tunius | ....................... | C09J 7/38 424/445 |
| 2013/0089581 A1 * | 4/2013 | Nielsen | ...................... | C08J 3/24 424/400 |
| 2013/0123678 A1 * | 5/2013 | Carty | ................... | A61F 13/0253 602/54 |

(Continued)

FOREIGN PATENT DOCUMENTS

CN 103937482 A 7/2014
EP 2371920 A1 10/2011
(Continued)

*Primary Examiner* — Guy K Townsend
(74) *Attorney, Agent, or Firm* — Coloplast Corp., Coloplast A/S; Nick Baumann

(57) ABSTRACT

Disclosed is a composition including a polymer and a switch initiator. The composition can be switched from a first liquid state to a second adhesive state by activation of the switch initiator. The composition has in the first liquid state a complex viscosity |η*| below 0.4 MPa s; and the composition has in the second adhesive state a second repeated peel force above 1 N/25 mm.

31 Claims, No Drawings

(56) References Cited

U.S. PATENT DOCUMENTS

| | | | | |
|---|---|---|---|---|
| 2013/0138062 A1* | 5/2013 | Klein | ...................... | A61F 5/443 604/336 |
| 2014/0213955 A1* | 7/2014 | Nielsen | ................ | A61L 24/043 602/54 |
| 2018/0008451 A1* | 1/2018 | Stroebech | ............... | A61L 24/06 |
| 2018/0021474 A1* | 1/2018 | Stroebech | ............... | A61F 5/443 604/336 |

FOREIGN PATENT DOCUMENTS

| | | | |
|---|---|---|---|
| JP | 1152180 | A2 | 6/1989 |
| JP | 2002501954 | A | 1/2002 |
| JP | 2002540817 | A | 12/2002 |
| JP | 2004527600 | A | 9/2004 |
| JP | 2005058288 | A | 3/2005 |
| JP | 2009227924 | A | 10/2009 |
| JP | 2013528829 | A | 7/2013 |
| WO | 9706836 | A2 | 2/1997 |
| WO | 9918136 | A1 | 4/1999 |
| WO | 0014131 | A1 | 3/2000 |
| WO | 0061692 | A1 | 10/2000 |
| WO | 0185077 | A1 | 11/2001 |
| WO | 04108175 | A1 | 12/2004 |
| WO | 2010034998 | A1 | 4/2010 |
| WO | 2013022898 | A1 | 2/2013 |
| WO | 2014028024 | A1 | 2/2014 |
| WO | 2014080954 | A1 | 5/2014 |

* cited by examiner

COMPOSITION COMPRISING A POLYMER AND A SWITCH INITIATOR

FIELD OF THE INVENTION

The present invention is within the field of polymer compositions comprising a switch initiator. The compositions may be for use as adhesive compositions to be applied to the skin. More particularly, the compositions may be for use as adhesives capable of attaching an ostomy device to the skin of an ostomy device user.

BACKGROUND

In connection with surgery for a number of diseases in the gastro-intestinal tract, one of the consequences in many cases is that the patient is left with an abdominal stoma, such as a colostomy, an ileostomy, or a urostomy, in the abdominal wall for the discharge of visceral contents. The discharge of visceral contents cannot be regulated at will. For that purpose, the user will have to rely on an appliance to collect the material emerging from such opening in a bag, which is later emptied and/or discarded at a suitable time. Ostomy appliances are typically attached to the skin of the ostomy user by means of an adhesive wafer on the ostomy appliance.

SUMMARY OF THE INVENTION

Embodiments provide a composition comprising a polymer and a switch initiator, wherein the composition can be switched from a first liquid state to a second adhesive state by activation of the switch initiator; the composition having in the first liquid state a complex viscosity $|\eta^*|$ below 0.4 MPa s (mega Pascal-second, i.e., MPa·s); and having in the second adhesive state a higher complex viscosity $|\eta^*|$ than the complex viscosity $|\eta^*|$ of the first liquid state, and having in the second adhesive state a second repeated peel force above 1 N/25 mm.

Embodiments provide a composition comprising a polymer and a switch initiator, wherein the composition can be switched from a first liquid state to a second adhesive state by activation of the switch initiator; the composition having in the first liquid state a complex viscosity $|\eta^*|$ below 0.4 MPa s; and having in the second adhesive state a second repeated peel force above 1 N/25 mm.

The viscosity of a mass or composition is a measure of its resistance to gradual deformation by shear stress or tensile stress. For liquids, it corresponds to the informal notion of "thickness". For example, honey has a higher viscosity than water. In the context of the present invention, viscosity is measured as described in detail herein. In particular, the indicated viscosity is the absolute value of the complex viscosity, i.e., $|\eta^*|$ measured at a frequency of 0.01 Hz.

A composition having in the second adhesive state a repeated peel force above 1 N/25 mm is advantageous because the peel force is sufficiently high to ensure that the adhesive in the second adhesive state remains properly attached to the substrate.

The present inventors have found that a composition having in the first liquid state a complex viscosity $|\eta^*|$ below 0.4 MPa s is advantageous in that it is capable of quickly flowing into the structure of a substrate, such as skin, and therefore is able to quickly wet the substrate and form a good basis for sufficient adhesion. Wetting means that the composition comes into direct contact with the surface of the substrate, including, where relevant, flowing into the micro and macro structures of the substrate.

In particular, within the field of pressure sensitive adhesives to be used for ostomy devices, our experiments have shown that a complex viscosity of 0.4 MPa s is the upper threshold for when a composition will flow sufficiently fast into the roughness of the skin and hereby obtain a desired adhesive contact in order to be able to seal around the stoma of a user within the period of time actually used by the average ostomy device user to attach the device.

In some embodiments, the composition in the second adhesive state has a second repeated peel force above a value selected from 1.5, 2, 2.5, 3, 3.5, 4, 4.5, 5, 6, 7, 8, 9, and 10 N/25 mm.

For instance, the second repeated peel force of the composition in the second adhesive state may be above 2.5 N/25 mm.

For instance, the second repeated peel force for the composition in the second adhesive state may be above 5 N/25 mm. A high peel force can help ensure low risk of detachment and, in relation to ostomy devices, leakage. For instance, a peel force of around 5 N/25 mm can be particularly advantageous when aiming at reducing the risk of leakage.

In some embodiments, the composition in the second adhesive state has a first peel force above 1 N/25 mm.

In embodiments, the first peel force and/or the second repeated peel force in the second adhesive state is below 15, such as below 10, such as below 5 N/25 mm. It can be advantageous to keep the peel force sufficiently low to ensure that the adhesive can be removed without leaving residue on the skin and or damaging the skin.

In some embodiments, the composition in the second adhesive state has a second repeated peel force that is at least 50% of the first initial peel force, such as at least 60%, at least 70%, at least 80%, at least 90%, or at least 95%. A relatively high second repeated peel force, as compared to the first peel force, shows that the adhesive composition is capable of maintaining its tacky and adhesive properties in the second adhesive state even after having adhered and once removed from the substrate. This is especially advantageous in situations where the adhesive is wholly or partly repositioned on the substrate during use. This may for instance be the case for ostomy adhesives adhered to the stomach skin of a user. During use, the skin will move and the ostomy adhesive will adapt as much as possible. However, the skin movements may cause parts of the adhesive to detach. In that situation, it is important that the adhesive retains tack and adhesion so that it can re-attach and remain securely adhered to the skin.

In some embodiments, the polymer is an acrylate polymer. In some embodiments, the polymer is an acrylate copolymer.

In some embodiments, the acrylate polymer or acrylate copolymer comprises monomer units selected from ethyl acrylate, butyl acrylate, ethylhexyl acrylate, hydroxyethyl acrylate, lauryl acrylate, and acrylic acid.

In embodiments, the polymer is a polyurethane.

In embodiments, the polyurethane comprises a diisocyanate selected from the group consisting of cycloaliphatic isocyanates, 4,4'-Methylenebis(cyclohexyl isocyanate) (HMDI), isophore diisocyanate, aromatic isocyanates, tolylene diisocyanate, 4,4'-diphenyl methyl diisocyanate (MDI), aliphatic isocyanates, and 1,6-hexane diisocyanate.

In embodiments, the polyurethane comprises a diol selected from the group consisting of polydimethylsiloxane (PDMS) based polyols, bis(hydroxyalkyl) terminated PDMS, and 4-{3-[bis(2-hydroxyethyl)amino]propoxy}-1-chloro-9H-thioxanthen-9-one (Thioxanthone diol).

In some embodiments, the switch initiator comprises a free radical generating switch initiator.

In some embodiments, the switch initiator comprises a photoinitiator. A photoinitiator is a moiety which, on absorption of light, generates reactive species, such as ions or radicals, and initiates one or several chemical reactions or transformations.

In some embodiments, the switch initiator is a photoinitiator selected from α-hydroxyketone, benzophenone, benzophenone derivatives, benzophenone/α-hydroxyketone, phenylglyoxylate, benzyldimethyl-ketal, aminoketone, acylphosphine derivatives, mono acyl phosphine (MAPO), MAPO/α-hydroxyketone, bis acyl ahosphine (BAPO), BAPO dispersion, BAPO/α-hydroxyketone, phosphine oxide, metallocene, ionium salt, thioxanthone, thioxanthone derivatives, mixture of triarylsulphonium hexafluorophosphate salts in propylene carbonate, mixture of triarylsulphonium hexafluoroantimonate salts in propylene carbonate, amphorquinone derivatives, benzil derivatives, anthraquinone derivatives, benzoin ether derivatives, polysilanes, and mixtures thereof.

In some embodiments, the switch initiator is a photoinitiator selected from 2-benzyl-2-(dimethylamino)-4'-morpholinobutyrophenone, 2-methyl-4'-(methylthio)-2-morpholinopropiophenone, (benzene) tricarbonylchronium, (cumene)cyclopentadienyliron(II)hexafluorophophate, dibenzosuberenone, ferrocene, methylbenzoylformate, and mixtures thereof.

In some embodiments, the switch initiator is the photoinitiator bis(.eta.5-2,4-cylcopenta-dien-1-yl)-bis(2,6-difluoro-3-(1H-pyrrol-1-yl)-phenyl) titanium (Ciba Irgacure 784).

In some embodiments, the activation of the switch initiator is caused by exposure of the switch initiator to light.

In some embodiments, the activation of the switch initiator is caused by exposure of the switch initiator to visible light and/or ultraviolet (UV) light. Visible light may be preferable in situations where it is important not to expose the adhesive and/or the skin of the user to UV light. Also, using a visible light switch initiator will make it possible to cause the switch "passively" by simply exposing the adhesive to normal daylight or light from regular indoor light sources. Using UV light can make it easier to control the switch in that normal daylight and regular indoor light sources will not lead to a switch.

In embodiments, the activation of the switch initiator is caused by exposure of the switch initiator to moisture. The moisture may be from the natural humidity of the air or it may be specifically provided, e.g., by applying water to the adhesive composition.

Compositions that contain a moisture switchable switch initiator are sometimes referred to as "moisture curing" compositions. This merely means that the switch takes place by exposure to moisture. Moisture curing and moisture switchable are used interchangeably herein.

In some embodiments, the composition in the first liquid state and/or the second adhesive state is adapted to handle moisture.

Adapted to handle moisture means that the composition has skin moisture handling capability, i.e., the composition is able to ensure that the amount of moisture accumulating on the surface of the skin is kept low. The composition could prevent such accumulation by being capable of absorbing moisture from the surface of the skin. The adhesive could also, or alternatively, be moisture vapor permeable, thereby ensuring that the moisture would permeate through the adhesive and away from the skin. Thus, in some embodiments, "adapted to handle moisture" means that the composition is moisture vapor permeable. In some embodiments, "adapted to handle moisture" means that the composition is absorbent, for instance by comprising a water absorbent material, such as a hydrocolloid. In embodiments, the composition is both absorbent and moisture vapor permeable.

In some embodiments, the composition in the first liquid state and/or the second adhesive state is adapted to handle moisture by being water absorbent.

In some embodiments, the composition comprises a water absorbent material.

In some embodiments, the composition comprises a water absorbent material in an amount of 1-60% (w/w) of the composition.

For instance, the composition comprises a water absorbent material in an amount of 1-40% (w/w) or 1-20% (w/w) or 20-40% (w/w) or 20-60% (w/w) or 40-60% (w/w) or 25-50% (w/w) of the composition.

In some embodiments, the water absorbent material is selected from hydrocolloid, water soluble salt, mono, di- and oligosaccharides, sugar alcohols, polypeptides, organic acids, inorganic acids, amino acids, amines, urea, super absorbent particles such as polyacrylic acid, glycols such as polyethylene glycol, fumed silica, bentone, bentonite, and mixtures thereof.

In some embodiments, the hydrocolloid is selected from guar gum, locust bean gum, pectin, potato starch, alginates, gelatine, xantan or gum karaya, cellulose derivatives, salts of carboxymethyl cellulose, sodium carboxymethyl cellulose, methyl cellulose, hydroxypropyl cellulose, hydroxyethyl cellulose, sodium starch glycolate, polyvinylalcohol, and mixtures thereof. Different absorbent materials will have different properties, such as rate of absorption and absorption capacity. For instance, guar gum or polyacrylic acid may be selected for their ability to maintain a relatively high cohesion of the adhesive composition even after significant absorption. On the other hand, carboxymethyl cellulose and similar compounds can be used to provide fast initial absorption rates and high absorption capacity.

In some embodiments, the water soluble salt is selected from NaCl, $CaCl_2$, $K_2SO_4$, $NaHCO_3$, $Na_2CO_3$, KCl, NaBr, NaI, KI, $NH_4Cl$, $AlCl_3$, $CH_3COONa$, $CH_3COOK$, HCOONa, HCOOK, and mixtures thereof.

In some embodiments, the composition in the first liquid state has an absorption of at least 0.1 $g/cm^2/2\ h$, such as an absorption in the first liquid state of at least 0.2, 0.3, 0.4, 0.5, 1, 1.5, 2, 2.5, or 3 $g/cm^2/2\ h$.

In some embodiments, the composition in the second adhesive state has an absorption of at least 0.05 $g/cm^2/2\ h$, such as an absorption in the second adhesive state of at least 0.06, 0.07, 0.08, 0.09, 0.1, 0.2, 0.3, 0.4, 0.5, 0.6, 0.7, 0.8, 0.9, or 1 $g/cm^2/2\ h$.

In some embodiments, the absorption of the composition in the first liquid state is higher than the absorption of the composition in the second adhesive state.

In some embodiments, the composition in the first liquid state and/or the second adhesive state is adapted to handle moisture by being moisture vapor permeable.

In some embodiments, the moisture vapor transmission rate (MVTR) of the composition in the first liquid state is above 250 $g/m^2/24\ h$, such as above 500, 750, 1000, 1250, 1500, 2000, 2500, or 3000 $g/m^2/24\ h$.

In some embodiments, the moisture vapor transmission rate (MVTR) of the composition in the second adhesive state is above 250 g/m²/24 h, such as above 500, 750, 1000, 1250, 1500, 2000, 2500, or 3000 g/m²/24 h.

In some embodiments, the composition in the second adhesive state has a G' in the range $10^3$-$10^5$ Pa or $10^3$-$10^4$ Pa or $10^4$-$10^5$ Pa, when measured as described herein at 1 Hz.

In some embodiments, the composition in the second adhesive state has a G" in the range $10^3$-$10^5$ Pa or $10^3$-$10^4$ Pa, when measured as described herein at 1 Hz.

In some embodiments, the composition in the first liquid state has a complex viscosity $|\eta^*|$ below 50 kPa s. Our experiments have shown that a pressure sensitive adhesive to be used within ostomy care with a complex viscosity below 50 kPa s will enable the adhesive to wet the peristomal skin of the user very fast—hereby quickly creating a large contact surface. In particular, all of the tested adhesive compositions with a complex viscosity $|\eta^*|$ below 50 kPa s exhibited wetting levels of at least 40% after 30 seconds and 100 g of pressure, measured as described herein. Such a wetting of at least 40% ensures that the adhesive composition very efficiently flows into the contours and microstructures of the skin and achieves a fast and strong bond. This is considered to be particularly advantageous in situations in which the device will be exposed to water or other liquids shortly after application, which is often the case for ostomy devices.

In embodiments, the composition in the first liquid state has a complex viscosity $|\eta^*|$ below 0.3 MPa s, below 0.25 MPa s, below 0.2 MPa s, below 0.1 MPa s, below 50 kPa s, below 10 kPa s, below 5 kPa s, below 1 kPa s, below 500 Pa s, below 100 Pa s, below 50 Pa s, below 10 Pa s, below 1 Pa s, in the range 0.1-0.4 MPa s, in the range 10-100 kPa s, in the range 1-10 kPa s, in the range 100-1,000 Pa s, in the range 10-100 Pa s, or in the range 1-10 Pa s.

In some embodiments, the composition in the first liquid state has a complex viscosity $|\eta^*|$ of at least 1, 10, 20, or 50 Pa s. Such a minimum viscosity will ensure that the composition remains viscous enough to be easily handled and that any particulate components of the compositions, such as hydrocolloids, can be evenly distributed and do not simply "sink" to the bottom of the composition. This will help ensure stability of the composition and make handling of the composition easier. In embodiments, the composition in the first liquid state has a complex viscosity $|\eta^*|$ of at least 100, 500, 1,000, 2,500, 5,000, or 10,000 Pa s.

In some embodiments, the complex viscosity in the second adhesive state is at least 2 times, such as at least 5 times, such as at least 10 times, such as at least 20 times, such as at least 50 times, such as at least 100 times, such as at least 1,000 times, such as at least 10,000 times higher than the complex viscosity in the first liquid state In some embodiments, the composition in the first liquid state has a lower cohesion than the composition in the second adhesive state.

In some embodiments, the composition is hydrophobic. In embodiments, the composition exhibits a water contact angle of at least 90 degrees. In embodiments the, water contact angle is at least 80 degrees.

In some embodiments, the composition is hydrophilic. In embodiments, the composition exhibits a water contact angle of less than 90 degrees.

In embodiments, the minimum or maximum water contact angles are the water contact angles of the adhesive polymer matrix (also referred to as the continuous phase) of the composition.

In some embodiments, the polymer forms a hydrophobic polymer matrix.

In some embodiments, the composition comprises hydrophilic material.

In some embodiments, the composition is a one-component composition.

In some embodiments, the composition is a switchable composition, i.e. a composition that has at least two states with different physical properties and that can be switched from one state to the other state. In some embodiments, the switch from one state to another state will be effected by activation of a switch initiator. A switchable adhesive composition may also be referred to as a "switchable adhesive."

In some embodiments, the composition is an adhesive composition.

Embodiments provide a method for securing a composition comprising a polymer and a switch initiator to the skin of a user, wherein the composition can be switched from a first liquid state to a second adhesive state by activation of the switch initiator; the composition having in the first liquid state a complex viscosity $|\eta^*|$ below 0.4 MPa s; and having in the second adhesive state a higher complex viscosity $|\eta^*|$ than the complex viscosity $|\eta^*|$ of the first liquid state, and having in the second adhesive state a second repeated peel force above 1 N/25 mm, the method comprising the steps of
  providing the composition in the first liquid state;
  applying the composition to the skin of the user; and
  activating the switch initiator, thereby switching the composition from the first liquid state to the second adhesive state and securing the composition to the skin of a user.

In embodiments, the composition is a composition as described herein. In embodiments, the composition is applied by the user to the user's own skin.

In some embodiments, the activation of the switch initiator comprises exposure of the switch initiator to light or moisture.

In some embodiments, the light comprises visible light and/or UV light. Visible light is defined as electromagnetic radiation with a wavelength in the range 400-700 nm. Ultraviolet light is defined as electromagnetic radiation with a wavelength in the range 10-400 nm.

In some embodiments, the exposure to light has a duration of 10-60 seconds.

For instance, the exposure to light may be less than 60 minutes, less than 30 minutes, less than 10 minutes, less than 5 minutes, less than 4 minutes, less than 3 minutes, less than 2 minutes, less than 1 minute, less than 45 seconds, less than 30 seconds, less than 15 seconds, less than 10 second, less than 5 seconds, 1-10 seconds, 10-30 seconds, 10-60 seconds, 30-60 seconds, 1-2 minutes, 2-3 minutes, 3-4 minutes, or 4-5 minutes.

In some embodiments, the activation of the switch initiator comprises uptake of moisture, e.g. from the surrounding air, into the adhesive composition.

Embodiments provide a composition comprising a polymer and a switch initiator, wherein the composition can be switched from a first liquid state to a second adhesive state by activation of the switch initiator; the composition having in the first liquid state a complex viscosity $|\eta^*|$ below 0.4 MPa s; and having in the second adhesive state a second repeated peel force above 1 N/25 mm.

In some embodiments, the composition is for securing a medical device, such as a wound dressing or an ostomy device, to the skin of a user.

An ostomy device can be suitable for use in connection with a colostomy, an ileostomy, or a urostomy. An ostomy device may be a closed appliance.

An ostomy device may be an open appliance. An open ostomy appliance is configured to be emptied while the appliance is attached to the skin of the user; typically through a drainage port in the bottom of the bag.

An ostomy device can be a one-piece appliance comprising a) a base plate (also referred to as a body-side member or face plate) attachable around the stomal opening; and comprising b) attached to the base plate a collection bag.

On ostomy device can be a two-piece appliance comprising a) a base plate (also referred to as a body-side member) attachable around the stomal opening; and comprising b) a separate collection bag attachable to the base plate. In this two-piece configuration, the collection bag can be replaced without replacing the base-plate attached to the skin around the stomal opening. The separate collection bag may be attached to the body side member in any convenient manner known per se, e.g., via a mechanical coupling, such as a coupling ring, or by an adhesive flange.

In embodiments, the composition is for securing the adhesive wafer of a two-piece ostomy device to the skin of a user. It may be advantageous to use the present composition in connection with a two-piece device, since the switching of the adhesive can be carried out without the presence of the collecting bag, which may be attached after the adhesive has been switched. This is particularly advantageous for compositions that are switched by application of light.

DETAILED DESCRIPTION OF THE INVENTION

One of the main concerns of people using ostomy appliances is that the ostomy adhesive attachment may be compromised resulting in leakage or even complete detachment of the ostomy appliance. Leakage is problematic not only in that it negatively affects the life quality of the ostomy device user but also because it will lead to skin problems. It is difficult to properly attach an adhesive to damaged skin, thus increasing the risk of further leakage and additional skin damage. There exists a need to further reduce the risk of leakage of ostomy devices.

A central challenge in the design of ostomy devices is that the device has to be attached to the skin of the ostomy device user. The skin is not an easy substrate for adhesion: It has a very large and highly irregular surface, it is often moist, and it stretches, bends, and moves as the ostomy user moves about. Also, many ostomy users have scar tissue in the area around the stoma.

Viewed in isolation, adhesion to the skin may be achieved in a number of ways. However, in the design of an adhesive suitable for use in an ostomy device, several other requirements should be considered. The ostomy adhesive should preferably be able to cope with the moisture evaporating from the skin underneath the ostomy adhesive. The ostomy adhesive should be able to stick to a moist surface, such as moist or sweaty skin, and should, after attachment, be able to somehow reduce accumulation of moisture at the skin surface. Accumulation of moisture at the skin surface can cause maceration of the skin, which is painful and which makes proper adhesion even more difficult to achieve. At the same time, it is of course preferable that the moisture and/or output from inside the collecting bag does not damage the adhesive or leak out to the surface of the ostomy user's skin.

In addition to adhering to the skin and handling moisture, an ostomy adhesive should also be able to remain attached to the skin while carrying a load, namely the collecting bag and its contents. Finally, ostomy adhesives should be able to be removed from the skin, while causing as little damage to the skin as possible and without disintegrating and/or leaving residue on the skin.

The present inventors have provided an adhesive composition, which is capable of preventing leakage by means of a combination of having a low viscosity in a first liquid state and being switchable to a second adhesive state with a sufficient peel force. The low viscosity ensures fast and good adhesion to the skin of a user and the sufficient peel force ensures that the adhesive remains securely attached and acts as a regular pressure sensitive adhesive during use. These effects combined lead to a lower risk of leakage from, e.g., an ostomy device attached with the instant adhesive composition.

In embodiments, the adhesive composition is adapted to prevent damage to the skin upon removal of the adhesive after use and/or upon repositioning of the adhesive during use. Damage to the skin may be in the form of stripping of the skin, meaning that skin cells are detached from the skin and removed together with the adhesive. Although some skin cells will usually detach from the skin and be removed together with the adhesive, excessive stripping of cells will lead to damage of the skin. Especially, if the skin is stripped of cells every time the adhesive is removed, this will result in painful damage to the skin and may compromise future adhesion to the damaged skin.

In embodiments, potential skin stripping is measured by attaching the adhesive composition to a paper substrate, such as a sheet of newspaper paper, and measuring the amount of paper fibre removed from the paper when the adhesive is removed. Removal of fibres from the paper will be an indication of the potential of the adhesive to cause stripping of the skin.

One way of looking at adhesion and risk of leakage is to consider leakage to be a result of a malfunctioning adhesive and/or an adhesive that has not been applied properly by the user. The present inventors have addressed both of these concerns. By providing an adhesive with a low viscosity, the adhesive will be easier to apply correctly in that it requires less manipulation by the user in order to properly flow into the skin surface. And by the combination of an adhesive that has flowed properly into the structure of the skin and at the same time has a sufficiently high second repeated peel force, it is ensured that the adhesive will also function properly once applied.

As will be appreciated from the above, the desired characteristics of an ostomy adhesive are many and sometimes contradictory. It should be able to handle moisture from the skin, but at the same time should be able to contain or resist any moisture from inside the collecting bag. This may be achieved by striking a good balance between absorption, permeability, and erosion resistance. The ostomy adhesive should be able to adhere properly and stay securely attached to the skin, but it should also be easy to remove without causing damage to the skin. This may be achieved by making sure the first and/or second repeated peel force of the adhesive is sufficiently high to stay attached without being so high as to cause pain upon removal. The repeated peel force after switch should be at least 1 N/25 mm, as measured herein. In embodiments, the first and/or second repeated peel force is below 10 N/25 mm, such as below 5 N/25 mm. A peel force below, e.g., 10 N/25 mm will help to ensure ease of removal of the adhesive composition and will also help prevent tearing of skin adjacent to the attachment site of the adhesive composition. Pain during removal may also be reduced by keeping the peel force low. A first and/or second repeated peel force below 5 N/25 mm may contribute further to these effects. Also, the low viscosity in the first liquid state will ensure that the composition flows well into the structure of the skin and quickly attains good adhesion.

Also, the ostomy adhesive is preferably soft so as to be comfortable on the skin of the user, and capable of adjusting to the movements of the user without detaching.

The adhesive used for ostomy appliances are typically pressure sensitive adhesives, meaning that application of pressure to the adhesive enhances the adhesive bond to the substrate, e.g., the skin. In several cases, ostomy bag users do not apply pressure enough to the adhesive base plate of the bag sufficiently to maintain the adhesive capabilities. By applying pressure to the pressure sensitive adhesive it is possible for the adhesive to wet and flow faster into the skin surface, hereby obtaining a large contact area and hereby increasing the experienced adhesive power. Current adhesive systems for attachment of ostomy device to the skin often require a high or prolonged pressure from the user in order to sufficiently flow into and wet the surface of the substrate.

Studies conducted by the inventors found that the time spent by ostomy users in applying the adhesive wafer to the skin varies a lot. In particular, 14 users where asked to apply an adhesive ostomy device to their own skin. The mean time used was around 30 seconds. The time spent in the experiment was as follows.

| % of users | Maximum time used (seconds) |
| --- | --- |
| 100.0% | 117 |
| 90.0% | 87 |
| 75.0% | 62 |
| 50.0% | 28 |
| 25.0% | 23 |
| 10.0% | 20 |
| 2.5% | 19 |

Instead of addressing the above problem by making the user apply more pressure—or pressure over an extended period of time—to the adhesive, the present inventors have found that it would be beneficial to construct an adhesive that takes into account the already existing application routine of users. In other words, the present inventors have aimed at constructing an adhesive composition that will work well with the current application routines of users rather than trying to change the habits of the ostomy users. The present inventors have found that there is a need to facilitate application of an ostomy device to the skin of the ostomy device user. Application should preferably be quick and straightforward, it should require as little strength and dexterity as possible, and it should result in a quickly established sufficient adhesion of the device to the skin of the user. The application should be straightforward and quick, even for elderly or disabled users.

In conclusion, the inventors have found that one challenge with typical pressure sensitive adhesives is that it takes a long time to achieve good adhesion to the skin. If a user cannot or does not allow the adhesive sufficient time to properly attach and for instance starts moving about before a good adhesion has been established, then this will increase the risk of the adhesive fully or partly detaching from the skin and, in the case of an ostomy device, leakage.

The inventors have further found that another challenge is that a pressure sensitive adhesive requires a certain amount of pressure in order to timely achieve proper wetting of a substrate and proper adhesion. It is difficult for disabled and elderly users to apply sufficient pressure, which increases the risk of insufficient adhesion and leakage. Also, properly applying a sufficient and even pressure over the entire surface of an adhesive is very difficult. This means that parts of the adhesive may receive insufficient pressure and therefore may not wet the skin properly and not achieve a sufficiently strong adhesion. In relation to ostomy devices, insufficient adhesion is an important contributing factor to the risk of leakage.

The present inventors have found that the many requirements of an adhesive can be addressed by using a composition that can exists in at least two different states, which have different physical properties and address different requirements of the adhesive. The composition can at some point be switched from one state to another state, thereby changing its physical properties and the characteristics associated with these properties.

For instance, a composition may have a first state in which it quickly and easily wets the surface to which it is to be adhered and thus achieves a sufficient adhesive attachment. The same composition may have a second state in which it very easily remains securely adhered to the skin and can be properly removed. In such a situation, the composition in its first state could be applied to the skin. Then the composition could be switched to the second state, in which it would remain securely attached.

The first state of the composition can be a first liquid state in which the composition is relatively fluid, i.e. has a low viscosity.

The second state can be a second adhesive state in which the composition possesses good adhesive qualities, for instance by exhibiting the characteristics of a pressure sensitive adhesive. In the present context, a pressure sensitive adhesive will exhibit a second repeated peel value, as measured herein, of at least 1 N/25 mm. The composition in the second state can be more viscous, i.e. have a higher viscosity, than the composition in the first state.

In general, the composition may be obtained by providing an adhesive and low-viscous substance and adding a switch initiator, which will make it possible to switch the adhesive from its first liquid state to its second adhesive state. The viscosity and other properties of the adhesive composition can be adjusted as indicated herein.

The composition can be a skin adhesive composition, i.e. an adhesive composition that is to be used on the skin of a person. The adhesive composition may for instance be used for attaching an ostomy device to an ostomy user.

By combining the properties of the first state and the second state into one composition, an adhesive is obtained that is capable of quickly and effortlessly establishing good adhesion and reliably staying adhered to the skin. The quick and effortless adhesion is achieved by the composition in the first state while the reliable adherence, for instance to skin, is achieved by the composition in the second state.

When applying an adhesive composition to a substrate it is advantageous to ensure that a proper adhesive bond is established between the adhesive composition and the substrate. One element in forming the adhesive bond is the flow of the adhesive composition into the micro- and macro-structure of the substrate. The better the adhesive composition is able to flow into, i.e. wet, the substrate, the larger the adhesive contact area obtained. A large contact area between the adhesive and the substrate will lead to improved adhesion. Wetting of a substrate by an adhesive composition is dependent on the characteristics of the composition as well as upon, e.g., time, temperature, and pressure. In relation to wetting of a substrate, a central characteristic of an adhesive composition is the viscosity, measured herein as the complex viscosity |η*|.

Embodiments provide an adhesive, which in a first state has a complex viscosity |η*| below 0.4 M Pa s. Viscosity is a measure of the resistance to gradual deformation of a given liquid state composition. Generally, the lower the viscosity, the more quickly the composition will be able to wet a rough surface by flowing into the small structures of the surface, such as the microstructure of skin.

In the present context, a relatively low viscosity in the first liquid state is advantageous in that it will lead to the composition more easily and quickly flowing into the contour of the skin.

An advantage of this low viscosity is that the adhesive in the first state will be able to easily and quickly flow into, i.e. wet, the microstructure of the skin as well as larger irregularities, such as scar tissue and wrinkles. This means that a large contact surface between the adhesive and the skin is quickly established and that a good adhesive bond between the skin and the adhesive is quickly obtained. Also, the establishment of the large contact surface is less dependent, or not dependent at all, upon the user applying pressure to the adhesive composition. In this manner, the composition will be less sensitive to the particular routine of the user in applying the composition to the skin. User studies have confirmed that individual users apply pressure very differently to ostomy adhesive plates. Even experienced users do not apply pressure evenly across the adhesive plate and often miss areas of the adhesive, which then may not adhere properly. Again, providing an adhesive that is less dependent on the exact user routine is advantageous.

Also, the adhesive in its first state will not require a lot of pressure from the outside in order for it to properly flow into the structures of the skin. Pressure sensitive adhesives, as the name implies, require pressure in order to obtain a good adhesion. A typical pressure sensitive adhesive is very viscous and will take a certain amount of time to properly flow into the structure of the skin. Applying pressure to the adhesive will aid in the adhesion process, but it may still take 10-60 minutes or even longer for the pressure sensitive adhesive to properly wet the structure of the skin and achieve sufficient adhesion. Using a composition with lower viscosity will reduce the time and effort, e.g., pressure, needed to achieve good wetting, a large contact surface, and a strong adhesive bond to the substrate, e.g., the skin.

The present inventors have found that the time and pressure necessary to achieve sufficient adhesion can be reduced by means of a composition as described herein. When the composition is used to attach an ostomy device, this means that the risk of leakage can be reduced because the composition in the first liquid state will be able to effectively wet the skin surface, thereby increasing the contact area between the composition and the skin and thus contributing to increased sealing between the composition and the skin.

Generally, in order to reduce the viscosity of a composition, low molecular weight compounds can be added to the composition, e.g. tackifiers, oils, monomers, oligomers, and plasticizers. Certain polymers, such as polyisobutylene, can be reduced in molecular weight by radiation. Also, generally low molecular weight polymers will be less viscous than higher molecular weight polymers.

Generally, the viscosity of a composition can be increased by choosing high molecular weight polymers or by cross-linking the polymer. Also, fillers, e.g. calcium carbonate, magnesium oxide, fumed silica, and lignin, can be added.

The viscosity is measured as described in detail herein. The measured viscosity correlates with the ability of the composition to flow into and wet a rough surface, such as skin. In particular, the indicated viscosity levels were measured at a frequency of 0.01 Hz, which is within the relevant frequency interval for bonding of adhesives to rough surfaces, such as skin. It has been suggested that a frequency of around 0.1 Hz is relevant for bonding of adhesive tapes to a smooth surface. The herein used slightly lower frequency of 0.01 Hz, corresponding to approximately 0.063 rad/s, reflects the experience of the inventors that an adhesive for a rough surface does not require quite as fast adhesion as a tape on a smooth surface and also needs a little more time to flow. In other words, the frequency of 0.01 Hz was chosen to reflect the somewhat slower process of skin adhesive bonding as compared to bonding to typical smooth substrates and thereby to get viscosity measurements that are as relevant as possible for an adhesive that is to be applied to the skin. The viscosity measurement therefore provide viscosity values that are relevant for the actual application to the skin of, e.g., an ostomy adhesive.

It is noted that the thickness of a layer of adhesive composition will play a role in the processes of, e.g., flow, wetting, and adhesion. In the context of ostomy adhesive, a layer of adhesive composition would preferably have a thickness in the range of 0.2-2.0 mm.

Once properly adhered to a substrate, it is advantageous that an adhesive is capable of remaining securely attached for as long as required. Also, it is advantageous that the adhesive can be properly removed. In relation to remaining securely attached, one important characteristic of an adhesive composition is the peel force.

Embodiments provide an adhesive, which in the second state has a second repeated peel force above 1 N/25 mm, measured as described herein.

An advantage of this is that the adhesive in the second state will act as a pressure sensitive adhesive and maintain a sufficiently strong adhesive bond with the substrate. In other words, the adhesive in the second state is not only attached by means of mechanical interlocking, such as that of epoxy glue or paint, but properly adhered to the substrate in such a way that the adhesive will retain adhesive strength even if detached and re-attached to a substrate.

The inventors have found that a repeated peel force in the second adhesive state of above 1 N/25 mm will allow the adhesive to behave in a manner similar to the most commonly used skin adhesives, e.g. ostomy adhesives that are on the market. In other words, the threshold value for repeated peel allows the user to experience at least the same level of security and comfort provided by the repeated peel forces of commercial non-switchable adhesives.

Peel force can be measured by applying a composition in a first liquid state to a substrate, switching the composition to its second adhesive state, and then peeling the composition off the substrate. This is what is referred to in the present context as a first peel force, or alternatively, a switched-on-substrate first peel force.

If the composition is applied, switched and peeled as described above, and then re-applied to the substrate and peeled off again, that second peel is what is referred to herein as the second peel force, or alternatively, the second repeated peel force, or sometimes the repeated peel force.

A peel force can also be measured by first switching a composition from its first liquid state to its second adhesive state, then applying the composition to the substrate, and then peeling the composition from the substrate. A peel force measured in this way would be referred to as a switched-off-substrate peel force.

In the present context, the composition in the second adhesive state should behave like a pressure sensitive adhesive. This means that the composition should adhere to the substrate not only by means of mechanical interlocking, but also by proper non-mechanical adhesion.

If the adhesive composition is attached merely by mechanical interlocking between the substrate and the adhesive, it may initially remain well attached to the substrate, but if the mechanical bond between substrate and composition is broken, the composition will not easily be able to re-attach to the substrate. In other word, the first peel force of a mechanically attached composition may be sufficiently high, but the second repeated peel force will certainly be very low and insufficient to secure maintained attachment to the substrate. Oftentimes, a purely mechanically attached composition cannot be re-applied to the substrate at all, following peel.

Thus, it may not be easy to distinguish mechanical interlocking from proper adhesion by looking solely at the first peel force. However, the second repeated peel force will clearly distinguish the two. In this way, the second repeated peel force is one measure of the pressure sensitive adhesive characteristics of the adhesive composition. A sufficiently high second repeated peel force will ensure that the composition acts in the second adhesive state as a pressure sensitive adhesive in that it can be peeled off, re-applied, and still remain securely adhered.

When used on skin, it can be advantageous that the adhesive bond to the skin is somewhat dynamic and that detachment and re-adherence is possible on both a small and a large scale. Body movements may cause detachment of the adhesive from small areas of the skin and in some cases, the user may want to detach, adjust, and re-adhere the adhesive. This applies particularly to adhesives used for ostomy and wound care applications. Thus, it is advantageous that such adhesives have the characteristics of a pressure sensitive adhesive in the second adhesive state, at least in that they can be detached and re-attached to the substrate.

Adjusting the second repeated peel force of a composition can be done, for instance, by adjusting the degree of cross-linking of the polymer used in the composition. The second repeated peel force can also be affected by adding tackifiers and/or plasticizers to the composition. Increasing the content of tackifiers and plasticizers will lead to an increased second repeated peel force. Correspondingly, a lower content of tackifiers and/or plasticizers will lead to a lower second repeated peel force. Depending on the exact choice of tackifiers and plasticizers, the repeated peel force can be adjusted without at the same time significantly affecting the viscosity of the composition. Polymers, which are more or less miscible with the base polymer of the composition, may also be added to control repeated peel. Hydrocolloids, oils, and various fillers can also be used to adjust the second repeated peel force. Generally, hydrocolloids and fillers will tend to reduce the peel force of the composition. The second repeated peel force is measured as described herein.

Viscoelastic properties of adhesive compositions, including viscosity as discussed above, can be determined by dynamic mechanical analysis. Other than viscosity, it can be relevant to consider the dynamic modulus, G, which is composed of the shear storage modulus G' and the shear loss modulus G".

The so-called Dahlquist-criterion propose that tack will not occur when the storage modulus of the adhesive is greater than $10^5$ Pa at room temperature. General purpose pressure sensitive adhesives, which have medium moduli and medium dissipation, generally have G' and G" in range of $10^4$ to $10^5$ Pa and $10^3$ to $10^5$ Pa, respectively.

For removable adhesives, in the low moduli and low dissipation region, G' and G" are both generally in the range of $10^3$ to $10^4$ Pa. For all of the Dahlquist-criterion measurements, the analysis is carried out at 1 Hz.

Thus, it may be advantageous to design an adhesive composition that fulfills the Dahlquist criterion in the second adhesive state.

Studies performed by the inventors have shown that the complex viscosity $|\eta^*|$ correlates well with the ability of an adhesive composition to wet a rough surface when applying a specified pressure. In particular, a low complex viscosity will result in a high percentage of wetting of a given substrate within a given time. Results show that a complex viscosity below 0.4 MPa s leads to good wetting of the surface of a given rough substrate within 30 seconds when using a setup and a load corresponding roughly to the situation of an ostomy user applying the adhesive wafer of an ostomy device to the skin.

The 30-second duration was chosen after the previously mentioned field study of 14 ostomy users, where the time spent by the users in applying the adhesive ostomy plate to the skin was measured. The median time spent was 28 seconds, with some users spending as little as 19 second and some as much as 117 seconds. The 30 seconds are thus within the typical range of time used by an ostomy user in applying the adhesive to the skin.

Further results from the wetting experiments have demonstrated that even lower complex viscosities will generally lead to a higher percentage wetting in the same set-up. In particular, all of the tested adhesive compositions with a complex viscosity $|\eta^*|$ below 50 kPa s exhibited wetting levels of at least 40% after 30 seconds and 100 g of pressure, measured as described herein. Such a wetting of at least 40% ensures that the adhesive composition very efficiently flows into the contours and microstructures of the skin and achieves a fast and strong bond. A current standard non-switchable skin adhesive used in ostomy care was measured by the present inventors to have a viscosity of around 2.5 MPa s and a wetting of around 30%.

Without being bound by theory, the present inventors hypothesize that a 40% wetting in the wetting test described herein corresponds to full wetting of the flat part of the substrate used in the test. This means that a wetting above 40% is a result of the adhesive having wetted at least some of the non-flat surfaces of the substrate. In other words, a wetting above 40% in the test indicates that the adhesive has flowed into the grooves of the substrate, thus demonstrating the ability of the adhesive to very quickly wet an uneven surface, such as skin.

Leakage can be measured, e.g., by means of a pressure-gradient test. In the pressure-gradient test, a circular adhesive is cut from a piece of adhesive between two release liners using a hollow-punch. One of the liners are removed from the adhesive and the circle is mounted in the centre of a circular PET-film. A stainless steel flange with a centre hole and a bent piece of stainless tubing soldered to one side of the centre hole is used as test fixture. A circular piece of substrate, such as pigskin, with a centre hole corresponding to the size of the central hole in the steel flange is mounted on the flange with glue. The remaining release liner is removed from the adhesive-PET construct and placed on the substrate. The assembled construct-substrate-flange is placed in a holder with the substrate in a horizontal configuration, and a specified weight is placed on top for a specified time to ensure good adhesion to the skin. The assembly is then placed in the test setup and a test liquid is placed in the tube with a syringe. The pipe is connected to the test setup with silicone tubing. A linear pressure gradient is applied through the silicone tubing and the pressure at which our test liquid is pressed all the way through the skin-adhesive interface is noted. A higher pressure corresponds to a higher resistance to leakage. The described leakage test is generally based on the test of ASTM F2392-04. Other methods of measuring leakage may also be used.

The shift between the different states of the composition is referred to herein as a switch.

Thus, the switch is the transition from one state to another state of a switchable composition. The duration of the switch will vary depending on, e.g., the nature of the switch initiator and the method of activation of the switch initiator. Generally, the switch will be a gradual process with a gradual change of physical properties of the material from one state to another state. In some instances, the switch will be very fast and the physical properties will change very quickly, e.g. within seconds, to those of the second state. In other instances, the switch will be slower and the change in properties will gradually happen over a period of, e.g., several minutes or even hours.

In embodiments, the physical properties of the adhesive in the first state are different from the physical properties of the adhesive in the second state. For instance, the viscosity and/or the modulus can be different in the first and second states of the adhesive. The switch may thus lead to a change in physical properties of the composition.

The cohesion of the composition may also change as a consequence of the switch. Typically, the switch will render the composition more cohesive, which will help ensure that an adhesive composition can be peeled from a substrate without leaving residue on the substrate, i.e. by adhesive failure and not cohesive failure. For a composition that is to be attached to the skin, it is highly advantageous that the composition can have a high adhesion to the skin and, at the same time, that it can be removed from the skin without leaving residue on the skin.

The switch is caused by activation of a switch initiator. The switch initiator is a component of the switchable composition and may, for instance, comprise or consist of a photoinitiator. The switch initiator can be activated by an external stimulus, such as by exposure to moisture or light, such as visible light and/or ultraviolet light. The switch initiator can work by one or more mechanisms, such as by generating free radicals. Thus, the switch initiator may be a free radical generating switch initiator. The free radical generating switch initiator may be a photoinitiator.

The activation of the switch initiator, such as activation of a photoinitiator, can lead to increased crosslinking of the polymer and/or increased molecular weight of the polymer.

The duration of the switch will vary depending on, e.g., the nature of the switch initiator and the method of activation of the switch initiator. Generally, the switch will be a gradual process with a gradual change of physical properties of the material from a one to another state. In some instances the switch will be very fast and the physical properties will change very quickly, e.g., within seconds. In other instances, the switch will be slower and the change in properties will gradually happen over a period of, e.g., several minutes.

In embodiments, the switch from the first liquid state to the second adhesive state is irreversible. In this context, irreversible means that once the composition has been switched to the second adhesive state, it cannot revert from that state back to the first liquid state. In embodiments, the switch is irreversible under normal conditions of use. It can be highly advantageous to have an irreversible switch because there is then no risk that the composition will "switch back" to a liquid state when it has been switched to the second adhesive state. For the user, it is important to have a feeling of security with the product. This feeling of security could be compromised if the user had a feeling or knew that the composition could, potentially at any time, switch back to the first liquid state.

In embodiments, the activation of the switch initiator comprises a transfer of material, such as water, into the composition.

In embodiments, the switch leads to a change in the chemical properties of the composition. For instance, the switch may lead to increased crosslinking or to other types of formation of covalent bonds. In embodiments, the activation of the switch initiator is active, in that it requires transfer of energy, such as light, or matter, such as moisture, into the adhesive compositions. In embodiments, the activation of the switch initiator is in the form of a chemical reaction. In embodiments, the chemical reaction is an exothermic reaction.

In embodiments, the composition comprises an acrylate, including methacrylates and their copolymers. Acrylate copolymers are especially preferred, e.g., alkyl acrylate copolymers.

The most commonly used monomers in polyacrylates include ethyl acrylate, butyl acrylate, ethylhexyl acrylate, hydroxyethyl acrylate, lauryl acrylate, and acrylic acid. They may be used singly or in a mixture, their relative proportions in the mixture being selected depending on the desired viscoelastic properties, glass transition temperature, compatibility etc.

The polymer may be a copolymer with one or more acrylates. Alternatively, the polymer may be a copolymer with one or more acrylates and a free radical polymerisable vinyl moiety. Such vinyl moieties include compounds such as itaconic anhydride, maleic anhydride or vinyl azlactone or glycidyl methacrylate.

The polymer may be a homopolymer, a random copolymer, or a block copolymer. The polymer may be branched or linear.

The composition may include bound-in curable moieties. Any conventionally known unsaturated compounds, e.g. olefinic or aromatic compounds may be used or compounds with labile groups or groups which can undergo free radical reactions, could be used as the curable molecules. Photoreactive groups may also be used and include groups such as anthracenes, cinnamates, maleimides and coumarin groups. Other functional groups include carboxyl, epoxy, urethane, siloxane, amides, and hydroxyl. Mixtures of all of the above may also be used. The bound-in curable groups may be end groups, pendant groups or may be incorporated into the backbone.

The polymer backbone may be partially cross-linked. Crosslinking can be achieved by incorporating monomers of e.g. N-methylol acrylamide, N-(iso-butoxymethylene)-acrylamide, methyl acrylamidoglycolate methyl ether (all 0.5-5% (w/w)) or metal chelates, e.g., acetylacetonates of Zr, Al, or Fe (up to 2% (w/w) of polymer weight), into the polymer backbone, which then crosslinks during drying after spreading on a substrate. Al and Ti acetylacetonates and similar compounds can also be added after polymerization in concentrations of 0.1-2% (w/w) and used as a crosslinker through utilizing carboxylic groups in the polymer backbone during the drying step.

Multi-functional isocyanates, like toluene diisocyante (TDI), trimethyl hexamethylene diisocyanate (TMDI), and hexamethylene diisocyante (HDI), can be used to chemically link hydroxylic or carboxylic functions of different polymer chains, added in concentration up to 1% (w/w).

Crosslinking can also be achieved between the carboxylic groups in the polymer backbone and added amino resins, such as derivatives of melamine, benzoguanamine, glycoluril, and urea, e.g., hexamethoxymethyl melamine, methoxymethyl methylol melamine, methoxymethyl ethoxymethyl benzoguanamine, tetrabutoxymethyl glycoluril, butoxymethyl methylol urea, in concentrations up to 6% (w/w).

The above mentioned cross-linking can also be achieved using polycarbodiimides or multifunctional propylene imines.

It is also possible to blend one or more polymers having high cohesive strength with one or more polymers having low cohesive strength in order to achieve the desired balance.

The polymer will most often be soluble in, and hence commercially supplied as solutions in, organic solvents such as ethyl acetate, hexane, toluene, acetone, etc. Preferably, the polymer is non-water-soluble.

The polymer may be a commercially available PSA or PSA precursor, e.g. acResin A 204 UV, acResin A 260 UV (BASF), Aroset 1450-Z-40, Aroset S390 (Ashland), GMS 788, GMS 1753 (Henkel).

The polymer may include curable molecules which may be low molecular weight monomers or oligomers. In the broadest sense, any conventional known unsaturated compounds, or compounds with labile groups or groups which can undergo free radical reactions, could be used as the curable molecules. Preferred examples, used alone or in mixtures, are curable molecules such as acrylic acid esters or methacrylic acid esters of alcohols, glycols, pentaerythritol, trimethylpropane, glycerol, aliphatic epoxies, aromatic epoxies including bisphenol A epoxies, aliphatic urethanes, silicones, polyesters and polyethers, as well as ethoxylated or propoxylated species thereof.

The curable molecules can have more than one unsaturated or reactive site. With more than a single functionality they enable chain extension. With multiple functionalities of three or greater they are able to form crosslinked three-dimensional polymeric networks. Examples include CN925 (Arkema), Ebecryl 870 (Allnex).

Preferably, the curable molecules and the polymer are soluble in each other when in the dry state, i.e., in the absence of a solvent. Alternatively, in the case that the polymer and the curable molecules are not mutually soluble in each other when dry, or are only partly mutually soluble, they are uniformly dispersed in the composition.

In embodiments, the composition comprises a polyurethane (PU). Polyurethanes are most commonly obtained by reacting molecules containing two or a higher number of alcohol functionalities with di- or polyisocyanates.

Among the organic diisocyanates that can be used in the synthesis of polyurethanes are: cycloaliphatic isocyanates such as 4,4'-Methylenebis(cyclohexyl isocyanate) (HMDI) and isophore diisocyanate, aromatic isocyanates such as tolylene diisocyanate and 4,4'-diphenyl methyl diisocyanate (MDI) as well as aliphatic isocyanates such as 1,6-hexane diisocyanate. Depending on the type of isocyanate used in the synthesis, different materials properties can be obtained. For example, the use of aromatic isocyanates leads to stiffer polymers with higher melting temperature. HMDI based hard segments are not very crystallisable, whereas MDI based hard segments will readily crystallize under favourable conditions. The symmetry of the hard segment is also relevant. Increasing symmetry favours the crystallization of the hard segment and increases the degree of phase separation, modulus, hardness, etc.

Among diols or polyols that can be employed in the synthesis of polyurethanes in the invention are: polydimethylsiloxane (PDMS) based polyols, such as bis(hydroxyalkyl) terminated PDMS, preferably with a weight averaged molecular weight ($M_w$) between 1,000-6,000 g/mol.

4-{3-[bis(2-hydroxyethyl)amino]propoxy}-1-chloro-9H-thioxanthen-9-one (Thioxanthone diol, depicted below) may be used in the synthesis of polyurethanes to impart a light induced crosslinking ability to the polymers.

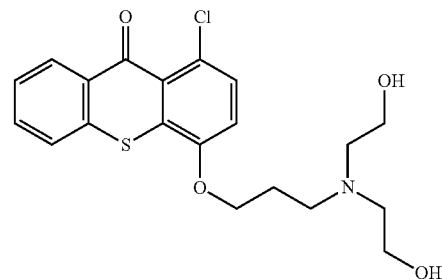 [SMILES: O=c1c2ccccc2sc2c(OCCCN(CCO)CCO)ccc(Cl)c12]

The thioxanthene diol is photo-reactive. In other words, it has the ability to absorb light and initiate free radical reactions, which will lead to crosslinked polyurethanes. The diol functionality in the photo-reactive group enables covalent bonding of these moieties into the polyurethane backbone. Photo-reactive groups built-in to the polymer have less probability to leach out from the polymeric material compared to the case where they are mixed into the polymeric material. This property may help ensure the biosafety of the polymer for direct skin use. Such built-in polymeric photo-initiators can create cross-links faster than photoinitiators that are simply mixed into the polymer. The photo-initiator mentioned here absorb light mainly in UV as well as to a small extent also in the visible region.

In addition to polyurethanes with built-in photo-reactive groups, polyurethanes with mixed-in photo-initiators are also of interest. Such materials can be prepared by mixing the photo-initiators such as thioxanthone without diol functionalization either during or after the synthesis of the polymer. In these cases, the photo-reactive moiety will not be part of the polyurethane. However, it will still initiate free radical reactions.

The rate of photo-induced crosslinking reaction and the polymer properties can be tuned by the composition of the polyurethane. The type and concentration of photo-initiator, presence of reactive groups as well as polymer mobility are among parameters, which determine the curing speed. The degree of crosslinking is a relevant parameter determining the final properties of the polymer. As the degree of crosslinking increases, the modulus of the polymer increases and mobility of the polymer decreases. The modulus affects the stickiness of the polymer, while mobility influences among various other properties the transport of molecules in the polymer. In case of ostomy care, transport of water molecules in the polymeric material can be an important factor.

In embodiments, the composition comprises a silicone polymer.

Moisture curing materials are polymeric materials that change from a liquid to a solid state when exposed to moisture. When these materials solidify, they are capable of sustaining deforming forces.

Moisture curing materials may comprise several components including a reactive polymer, a catalyst, a viscosity modifier, a crosslinker, and a water scavenger. The function of the reactive polymer together with a catalyst and a crosslinker is to form a polymer network upon exposure to moisture. This event makes moisture curing materials change from a liquid to a solid state. This may be referred to as "switching" or "curing".

The function of a viscosity modifier is to tune the viscosity to fulfill the requirements of each application. The function of the water scavenger is to prevent unintended curing in the container.

Moisture curing materials may be in one part or in two parts. In case of one-part moisture curing materials, all components may be mixed and stored in a single container until use. Curing starts only once the moisture curing material is open and exposed to moisture. On the other hand, in case of two-component systems, reactive components are isolated from each other in different containers during storage, and come into contact only at the time of use. The reactive components are mixed shortly before use. Curing starts as soon as the reactive components are mixed.

The change of properties from liquid to an adhesive state in moisture curing materials is usually based on condensation cure chemistry.

There is a variety of base polymers with different backbone chemistries, which can lead to condensation cure. Silicone polymers may be used in condensation cure compositions. In order to react via condensation cure, silicones may be terminated with hydroxyl groups in both ends. In the presence of a multifunctional silane, which acts both as cross-linker and water scavenger, catalyst and moisture, hydroxyl terminated silicones will cure. The reactivity of silanol groups vary with the number of electron-withdrawing groups substituents on the silicon atom.

The substituents on the multifunctional cross-linker is a relevant parameter, which may affect the cure speed. A trifunctional, tetrafunctional, and even higher functional oligomeric and polymeric cross-linkers can be employed. In embodiments, different substituents, such as methyl, ethyl, and vinyl groups may be used. Examples of trifunctional cross-linkers based on alkoxy groups include methyl trimethoxy silane and methyl triethoxy silane. In addition to alkoxy, acetoxy, oxime, amine, amide, and enoxy cure systems are available.

The curing systems may be adapted to different applications depending on by-products of the curing process. For example, for ostomy care, by-products should be non-toxic and should not have a bad smell.

A suitable condensation cure catalyst is chosen depending on the chemistry of the multifunctional silane. Titanates are employed with alkoxy, amide, or oxime systems, whereas tin catalysts may be added to acetoxy, oxime, and amine cure formulations. In embodiments, the titanate catalyst used is selected from tetraalkoxy titanates and chelated titanates. Tetraalkoxy titanates are the more catalytically active species.

The rate of condensation curing depends on the cross-linking agent (its functionality, concentration and chemical structure), the type of catalyst, and the relative humidity of the environment.

Moisture curing formulations are interesting materials for applications in ostomy care, either as an accessory or as a full device. Some relevant features to consider for moisture curing compositions to be used in ostomy care:

Safe to use on skin: Moisture curing formulations should be non-toxic before and after cure since they will meet skin.

Adhesion to skin: Moisture curing formulations should adhere to skin before and after cure. Otherwise, these materials will provide a weak interface between the skin and ostomy care device.

Handle moisture from body: Ostomy care products should handle moisture, which comes from skin, output, and sweat. Otherwise, water remaining on the skin weakens the adhesion.

Stable during storage: Moisture curing formulations should be stable during storage in the factory and transportation, but also in the hands of the users before use. Depending on the geographic location, the temperature, and relative humidity of the environment changes. Moisture curing formulations should be stable enough not to cure when exposed to temperatures relevant to storage, transportation, and use situation. In addition, they should be packaged in a way that the moisture cannot diffuse into their container.

Commercially available moisture curing formulations used, e.g., in the construction industry are typically not safe for use on skin. The commercially available "Trio Silken Stoma Gel" from Trio Healthcare is approved for use on skin. However, Trio Silken Stoma Gel has major shortcomings, since it does not adhere to skin and does not absorb body fluids.

Typically, moisture-curing materials for ostomy care applications include a reactive component to cure, a water absorbing component to absorb moisture from the body, and an adhesive component to enable skin adhesion. A straightforward strategy to obtain skin adhesives based on moisture curing is to mix unreactive polymers with adhesive character with reactive components, which on their own do not adhere to skin before and after cure. Such materials will be adherent to skin before and after cure. Employing such a strategy opens the opportunity of using a variety of reactive materials available in other industries after necessary modifications to fulfill the bio-safety requirements for skin application. As the water-absorbing component, e.g., natural hydrocolloids or synthetic hydrophilic polymers can be used.

Adding a water-absorbing component to moisture curing formulations may lead to additional considerations, since some water may be present in natural hydrocolloids or synthetic hydrophilic polymers, which may cause undesired effects with regard to both curing speed and storage stability. A way to minimize such effects is careful drying of water absorbing components prior to their addition to moisture curing formulations.

A switch initiator is a component of a switchable composition, which component upon activation is able to trigger a switch of the switchable composition.

In embodiments, the switch initiator comprises or consists of a free radical generating switch initiator. The free radical generating switch initiator may be a photoinitiator. Different photoinitiator systems exist. Photoinitiator systems can be (a) low molecular weight single component, (b) low molecular weight multiple component, (c) polymeric single component, or (d) polymeric multi-component. These systems can be built using chemicals named below and/or polymers containing these functionalities.

In the present invention, a photoinitiator is defined as a moiety, which, on absorption of light, generates reactive species (ions or radicals) and initiates one or several chemical reactions or transformation. In some embodiments, a preferred property of the photoinitiator is good overlap between the UV light source spectrum and the photoinitiator absorption spectrum. In some embodiments, a desired property is a minor or no overlap between the photoinitiator absorption spectrum and the intrinsic combined absorption spectrum of the other components in the composition, e.g., the absorption of the polymer matrix or any absorbent materials and fillers in the composition.

Suitably, the photoinitiator moieties are pendant on the polymer. This means that they are attached to the polymer at points other than at the polymer ends, thus making it possible to attach more than two photoinitiator moieties to a single polymer.

In embodiments, the composition comprises a built-in photoinitiator. In embodiments, the composition comprises a free or mixed-in or non-built-in photoinitiator. In embodiments, the composition does not comprise a free or mixed-in or non-built-in photoinitiator. In embodiments, the composition does not comprise a built-in photoinitiator. Examples of built in photoinitiators include Dymax 1072-M from Dymax Corp. and Rahn Genopol TX-2 from Rahn Corp.

The photoinitiator moieties of the invention may independently be cleavable (Norrish Type I) or non-cleavable (Norrish Type II). Upon excitation, cleavable photoinitiator moieties spontaneously break down into two radicals, at least one of which is reactive enough to abstract a hydrogen atom. Benzoin ethers (including benzil dialkyl ketals), phenyl hydroxyalkyl ketones and phenyl aminoalkyl ketones are examples of cleavable photoinitiator moieties.

In embodiments, the photoinitiator is efficient in transforming light from the UV or visible light source to reactive radicals, which can abstract hydrogen atoms and other labile atoms from polymers, and hence effect covalent cross-linking. Optionally, amines, thiols and other electron donors can be either covalently linked to a polymeric photoinitiator or added separately or both. The addition of electron donors is not required but may enhance the overall efficiency of cleavable photoinitiators according to a mechanism similar to that described for the non-cleavable photoinitiators below.

In embodiments, the photoinitiator of the invention is non-cleavable (Norrish Type II). Non-cleavable photoinitiators do not break down upon excitation, thus providing fewer possibilities for the leaching of small molecules from the composition. Excited non-cleavable photoinitiators do not break down to radicals upon excitation, but abstract a hydrogen atom from an organic molecule or, more efficiently, abstract an electron from an electron donor (such as an amine or a thiol). The electron transfer produces a radical anion on the photoinitiator and a radical cation on the electron donor. This is followed by proton transfer from the radical cation to the radical anion to produce two uncharged radicals; of these, the radical on the electron donor is sufficiently reactive to abstract a hydrogen atom.

Benzophenones and related ketones such as thioxanthones, xanthones, anthraquinones, fluorenones, dibenzosuberones, benzils, and phenyl ketocoumarins are examples of non-cleavable photoinitiators. Most amines with a C—H bond in α-position to the nitrogen atom and many thiols will work as electron donors. An advantage of using Norrish Type II as opposed to Type I photoinitiators is fewer generated by-products during photoinitiated reactions. As such, benzophenones are widely used. When for example α-hydroxy-alkyl-phenones dissociate in a photoinitiated reaction, two radicals are formed, which can further dissociate and possibly form loosely bound unwanted aromatic by-products.

Self-initiating photoinitiator moieties may also be used. Upon UV or visible light excitation, such photoinitiators predominantly cleave by a Norrish type I mechanism and cross-link further without any conventional photoinitiator present, allowing thick layers to be switched. Recently, a new class of β-keto ester based photoinitiators has been introduced.

In some embodiments, the switch initiator comprises at least two different types of photoinitiators. The absorbance peaks of the different photoinitiators are at different wavelengths, so the total amount of light absorbed by the system increases. The different photoinitiators may be all cleavable, all non-cleavable, or a mixture of cleavable and non-cleavable. A blend of several photoinitiator moieties may exhibit synergistic properties. In some embodiments, the switch initiator comprises a mix of different photoinitiators, such as two, three, four, or five different photoinitiators.

Examples of photoinitiators absorbing in the 200-400 nm range include α-hydroxyketone, benzophenone, benzophenone derivatives, benzophenone/α-hydroxyketone, phenylglyoxylate, benzyldimethyl-ketal, aminoketone, acylphosphine oxide derivatives, mono acyl phosphine (MAPO), MAPO/α-hydroxyketone, bis acyl phosphine (BAPO), BAPO dispersion, BAPO/α-hydroxyketone, phosphine oxide, metallocene, ionium salt, thioxanthone derivatives, mixture of triarylsulphonium hexafluorophosphate salts in propylene carbonate, mixture of triarylsulphonium hexafluoroantimonate salts in propylene carbonate, camphorquinone derivatives, benzil derivatives, anthraquinone derivatives, benzoin ether derivatives, and polysilanes.

Specific examples of photoinitiators include 2-Benzyl-2-(dimethylamino)-4'-morpholinobutyrophenone, 2-Methyl-4'-(methylthio)-2-morpholinopropiophenone, (Benzene) tricarbonylchronium, (Cumene)cyclopentadienyliron(II) hexafluorophophate, dibenzosuberenone, ferrocene, and methylbenzoylformate.

Other examples include aromatic ketones useful in the 200-400 nm range, e.g. acetophenone; camphorquinone+iodonium salt+silane (which may be useful in obtaining efficient photoinitiation in air); peroxides, e.g. benzoyl peroxide; and azo compounds, e.g. 2,20-azobisisobutyronitrile.

In the >400 nm range examples of photoinitiators include carbazole derivatives, metallocene, thioxanthone derivatives, camphorquinone derivatives, benzil derivatives, titanocenes, anthraquinone derivatives, acylphosphine derivatives, keto-coumarins, xanthenic dyes (e.g. erythhrosin B), thioxanthone derivatives (e.g. 2-chlorothioxanthone, 2-isopropylthioxanthone, 2-mercaptothioxanthone, thioxanthone acetic acid derivatives) optionally in combination with amines, and benzophenones optionally in combination with amines.

In embodiments the switch initiator comprises or consist of bis(.eta.5-2,4-cylcopentadien-1-yl)-bis(2,6-difluoro-3-(1H-pyrrol-1-yl)-phenyl) titanium (Ciba Irgacure 784).

In embodiments, the composition comprises a switch initiator, which is sensitive to moisture. A moisture sensitive switch initiator will cause the composition to switch from a first state, such as a first liquid state, to a second state, such as a second adhesive state, when the moisture sensitive switch initiator is exposed to moisture.

In embodiments, the switch initiator comprises or consists of a moisture sensitive switch initiator. In embodiments, the moisture sensitive switch initiator comprises or consists of a polymer.

In embodiments, the switch initiator comprises or consists of a moisture sensitive silicone polymer, such as Trio Silken (Trio Healthcare).

In general, moisture switchable composition can comprise an unreactive and tacky silicone polymer, such as BIOPSA, and a reactive non-tacky silicon polymer, such as the Trio Silken polymer exemplified herein. In this way, the different functions of crosslinking and tackiness are provided by different polymers, and switching speed and level as well as tack can be adjusted separately. In this manner, switching speed and level can be appropriately modified without compromising tack.

It has been reported that humans for short periods can sweat more than 20,000 g/m$^2$/24 h. Thus, the moisture handling ability of skin adhesives, e.g. the water absorption capacity and the moisture vapour transmission rate (MVTR) of the adhesive, is relevant to the performance of the adhesive.

For a number of reasons, moisture-handling capability is especially relevant for an adhesive used to attach an ostomy device: The adhesive used to attach the ostomy device is placed on approximately the same area of skin around the stoma every day for weeks, months, or years. Thus, the health of this particular area of skin is very important. An adhesive that properly handles moisture will contribute to the health of the skin by keeping the skin relatively dry and thus preventing macerations and other moisture-related damage to the skin. Furthermore, an excessive accumulation of moisture between the skin and the adhesive will lead to a weakened bond of the adhesive to the skin. This is especially problematic for an ostomy device, which has to be able to carry a load and stay very firmly attached to the skin to prevent leakage.

The moisture handling ability of a composition can be controlled for instance by making the composition capable of absorbing water and/or by making the composition moisture vapor permeable. A composition can at the same time be both absorbent and moisture vapor permeable, for instance by including hydrocolloids or other absorbing materials in a moisture vapor permeable composition.

One way of rendering a composition capable of handling moisture is by including absorbent material in the composition. The absorbent material can for instance be a water-soluble or water swellable material and can be added in an amount sufficient to ensure proper handling of the moisture present at the site of the adhesive.

The water absorbent material is suitably a particulate, solid water absorbent hydrophilic agent, such as a water-soluble or a water swellable (non-water soluble) hydrocolloid. The water soluble or water swellable (non-water soluble) hydrocolloids may suitably be selected from natural or synthetic hydrocolloids, such as guar gum, locust bean gum, pectin, alginates, gelatine, xantan or gum karaya, cellulose derivatives (e.g. salts of carboxymethyl cellulose such as sodium carboxymethyl cellulose, methyl cellulose and hydroxypropyl cellulose), sodium starch glycolate, polyvinylalcohol, polyacrylic acid (e.g. In the form of super absorbent particles SAP), and polyethylene glycol. Suitable hydrocolloids are, e.g., AQ 1045 (a branched water dispersible polyester) from Eastman, Pectin LM 12CG Z or Pectin USP/100 from CP Kelco, Natrosol (hydroxyethyl cellulose, non-ionic, water soluble ethers of cellulose and ethylene oxide) produced by AQUALON, Blanose 9H4XF (carboxymethyl cellulose) available from Hercules, Akucell® AF 2881 (carboxymethyl cellulose) available from Akzo, AquaSorb® (cross-linked carboxymethyl cellulose) from Aqualon, Sorbalg pH 470 (Calcium alginate) from Danisco Ingredients, Denmark. The hydrocolloids may also be selected from microcolloids (e.g having a particle size less than 20 microns or preferably below 5 or 2 microns).

The absorption capacity of a composition can be measured as defined herein. The water absorption capacity can be measured in one or both of the first and second states of the composition. The water absorption may be the same or different between the first and second states of the composition. In some embodiments, the water absorption capacity is higher in the first state than in the second state. In other embodiments, the water absorption capacity is lower in the first state than in the second state of the composition. A good absorption capacity will make the composition capable of handling moisture on the skin and will thereby prevent accumulation of moisture between the skin and the adhesive and thus help prevent damage to the skin, such as maceration.

As an alternative or a supplement to making the composition capable of handling moisture by adding water absorbent materials, the composition can be capable of handling moisture by being moisture vapor permeable. Acrylate compositions can be moisture vapor permeable and examples are provided herein of acrylate compositions with varying degrees of moisture vapor permeability.

The moisture vapor permeability of a composition can be measured by measuring the moisture vapor transmission rate (MVTR) as described herein. In some embodiments, the composition in the first liquid state and/or in the second adhesive state has an MVTR above 500 g/m$^2$/24 h measured as described herein.

In some cases, it is desirable to reduce the amount of absorbing material in a given composition. This can be because a high amount of, for instance, hydrocolloids may lead to the composition becoming too hard and/or too easily eroded. In those cases, a moisture vapor permeable composition is advantageous in that it can render a composition with no absorbing material, or a relatively low amount of absorbing material, capable of handling moisture.

Moisture vapor permeable compositions can contain absorbing materials to supplement the moisture handling effect of the moisture vapor permeable composition as such. A composition comprising absorbing material and at the same time being moisture vapor permeable may be advantageous in that the positive effects of absorption and moisture vapor permeability are combined in one composition.

The pressure sensitive adhesive used according to the invention may contain other conventional ingredients for compositions, such as tackifiers, extenders, non-reactive polymers, oils (e.g. polypropyleneoxide, ethyleneoxide-propyleneoxide copolymers, and mineral oil), plasticizers, fillers, surfactants. The adhesive may also comprise pharmaceutically active ingredients. These optional ingredients may be present in the reaction mixture during the cross linking reaction.

Measurement Methods

Dynamic Mechanical Analysis (DMA) and Determination of G', G'', tan(δ), and Complex Viscosity |η*|

The parameters G', G'', tan(δ), and complex viscosity |η*| were measured as follows by a frequency sweep. The adhesives were pressed into a plate of 1 mm thickness. A round sample of 25 mm in diameter was cut out and placed in a Haake RheoStress 6000 rotational rheometer from Thermo Scientific. The geometry applied was parallel plates 25 mm and the shear stress was fixed at 5556 Pa and a gap size of 0.9-1.05 mm was applied to the sample in the beginning of the measurement to obtain a normal force of approximately 5 N. The measurements were carried out at 32° C.

For the complex viscosity |η*| the value measured at a frequency of 0.01 Hz was used. The test was run as a frequency sweep from 100 Hz to 0.01 Hz.

Peel Force

A sample of 25×100 mm was cut from the prepared sheet composition and a 25×300 mm piece of auxiliary tape was then added on the top of the sample. After 30 minutes of conditioning at 23° C. and 50% relative humidity, the sample was mounted in a tensile testing machine (INSTRON 5564 from Instron) and a 90-degree peel test was carried out from a Teflon substrate at a speed of 304 mm/min. The results are given in N/25 mm.

If required for the particular measurement, the samples were switched as described herein below for the individual compositions. The light curing materials that were not to be switched were covered with a light occlusive tape.

Samples were either attached to a substrate and peeled without having been switched at all ("non-switched"), attached to the substrate, then switched, and then peeled ("$1^{st}$ peel, switched on substrate"), attached to a substrate, then switched, then peeled, and then re-attached and peeled a second time ("$2^{nd}$ repeated peel, switched on substrate"), or first switched, then attached to the substrate, and then peeled ("peel when switched off substrate").

For the $2^{nd}$ repeated peel, switched on substrate, an additional 30 minutes of conditioning at 23° C. and 50% relative humidity was used before performing the second repeated peel.

The peel test was carried out in a climate-controlled room at 23° C. and 50% relative humidity. Peel angle was fixed at 90° and the peel speed was 304 mm/min. Dwell time, meaning the time the sample is rested before testing, was 30 minutes.

The Teflon substrate (2.0 mm PFTE, order no. SPTFE0020INA from RIAS, Roskilde, Denmark) mounted in steel plate was attached to the peel sledge. Adhesive strips were punched out from 0.4 mm thick adhesive sheets in the dimensions 25×100 mm. Auxiliary tape (25 mm width) was mounted on the adhesive with 10 mm overlap. The release liner was lifted in one end to make the overlap with the auxiliary tape. The adhesive was applied to the substrate by using an automatic roll with a load of 2 kg. The average of the mean load was reported as N/25 mm. The failure type, i.e. cohesive or adhesive failure, was observed, recorded, and reported with the peel data.

Moisture Vapour Transmission Rate

Moisture vapour transmission rate (MVTR) is measured in grams per square meter ($g/m^2$) over a 24 hours period using an inverted cup method.

A container or cup that was water and water vapour impermeable having an opening of Ø35 mm was used. 20 mL saline water (0.9% NaCl in demineralised water) was placed in the container and the opening was sealed with the test adhesive mounted on a highly permeable polyurethane (PU) backing film (BL9601 foil from Intellicoat). The container was placed into an electrically heated cabinet and the container or cup was placed upside down, such that the water was in contact with the adhesive. The cabinet was maintained at 32° C. The film reference is used in all experiments to control for any variations in testing conditions.

The weight loss of the container was followed as a function of time. The weight loss was due to water transmitted through the adhesive and/or film. This difference was used to calculate the MVTR of the test adhesive film. MVTR was calculated as the weight loss per time divided by the area of the opening in the cup ($g/m^2/24$ h).

The MVTR of a material is a linear function of the thickness of the material. Thus, when reporting MVTR to characterize a material, it is important to inform the thickness of the material which MVTR was reported.

Finally, we noted that by using this method, we introduced an error by using a supporting PU film. Utilizing the fact that the adhesive/film laminate was a system of two resistances in series eliminated the error. When the film and the adhesive are homogeneous, the transmission rate may be expressed as:

$$1/P(\text{measured}) = 1/P(\text{film}) + 1/P(\text{adhesive}).$$

Hence, by knowing the film permeability and thickness of the adhesive, it is possible to calculate the true permeability of the adhesive, P(adhesive), using the following expression:

$$P(\text{adhesive}) = d(\text{adhesive})/150\ \mu m * 1/(1/P(\text{measured}) - 1/P(\text{film})),$$

where d(adhesive) was the actual measured thickness of the adhesive and P(film) was the MVTR of the film without any adhesive on and P(measured) was the actual measured MVTR.

Moisture Absorption

Samples were prepared by thermoforming to a 0.5 mm thick adhesive film between two release liners. With a punching tool, samples were punched out. Sample size was 25×25 mm. The release liners were removed. The samples were glued to an object glass and placed in a beaker with physiological salt water and placed in an incubator at 37° C.

The sample was weighed at the outset (M(start)) and after 2 hours (M(2 hours). Before weighing, the object glass was dried off with a cloth. For a 25×25 mm sample the area was 6.25 $cm^2$ (the surface edges were left out of the area). The moisture absorption may be calculated as: Water absorption after 2 hours=(M(2 hours)−M(start))/6.25 $cm^2$. The result is in the unit $g/cm^2$ per 2 hours.

Erosion Resistance

Erosion resistance is a measurement of how well the adhesive composition is able to resist breakdown when being exposed to moisture. Adhesive compositions capable of handling moisture are typically absorbent to some degree. The absorption will ensure that moisture on, e.g., the skin of a user is absorbed into the adhesive and thereby away from the skin surface where it might cause damage. Too much absorption, however, may destabilize the adhesive in that excessive swelling of the adhesive leads to decreased cohesion. As such, it is preferable to balance the absorption and cohesion of the adhesive composition. An adhesive with a well-balanced relationship between absorption and cohesion will typically exhibit a good resistance to erosion. A disk of the composition having a thickness of 0.5 mm, an outer diameter of 55 mm, and a hole of diameter of 25 mm was coated on the top surface with an impermeable low-density polyethylene (LDPE) film.

The other side of the composition was attached to the surface of a dish by means of a double sided adhesive tape and the system was mounted in a 1 l jar in an upright position in the middle of the jar. The jar was half filled with 0.9 wt-% NaCl in demineralised water and closed with a lid. The jar was placed in a lying position between two rollers and was rolled with a speed of 20 rpm in one direction and 20 rpm in the other direction for each 1 minute. If erosion was seen as a result of missing material this was noted. Also, the swelling (in one side) in mm was measured and the result reported as the average of two independent measurements. This result of this erosion measurement is an indication of the resistance to water. All data is measured after 24 hours. The test was done at 20° C.

Wetting

A wetting test was set up to observe the flow of an adhesive into the valleys of rough surface of that like a skin. By utilizing a transparent material for making the rough substrate, it was possible to observe the flow of an adhesive in to the roughness of a substrate. Hereby it was made possible to quantify the wetting characteristics of an adhesive with a specified load applied to it.

User studies have shown that ostomy users apply pressure quite unevenly and with very different force to an ostomy adhesive wafer. At the lower end of the scale in terms of applied pressure, an ostomy user will apply approximately 5.5 kPa of pressure to the contact area between the adhesive wafer of the ostomy device and the finger applying the pressure. This corresponds to applying a 100 g load on an area the size of a fingertip (approximately 15 mm in diameter). As explained herein, recordings of the duration of the application routine have shown that this pressure is applied within a timeframe of approximately 30 seconds.

These observations were used to design an adhesive that will perform in a real-life situation as an ostomy adhesive, even for ostomy users that apply only a very limited pressure to the adhesive wafer.

The observations were also used as the background for designing the instant wetting experiment to properly reflect the performance of an adhesive in the real-life setting of attachment of an ostomy device to the skin of a user.

Procedure

Mount rough substrate to glass slide
Mount adhesive to load
Apply adhesive with load onto substrate
Take picture through back side of system
Post process each picture to be able to observe contact vs. non-contact and make black and white accordingly
Count number of black pixels in each picture Materials Microscope with picture taking capabilities
Glass slides (transparent)
Rough substrate
100 g load with Ø15 mm contact area
Adhesive sample Testing Conditions 32° C.
20% relative humidity Substrate An acrylic plate with a rough surface and an opposing non-rough surface that was 1.30 mm thick and had a diameter of 20 mm was used for determining the flow of an adhesive into the valleys of a rough substrate.

The roughness in one side of the substrate was made of small triangular grooves running in the two axis of the surface plane. The triangles were oriented so that bottom side of the triangle is coincident with the top surface of the substrate thereby making a wedged groove in to the substrate. The triangles were right sided triangles with a width and a height of 0.15 mm. The grooves were repeated with spacing from centre to centre of the triangles of 0.35 mm.

The substrate was placed with the non-rough surface on a transparent glass slide using a cyanoacrylate adhesive to fixate the substrate and improve the optical transparency of the non-rough surface of the substrate.

The glass slide with the rough substrate was placed above a microscope with the free glass surface facing the microscope in order to observe through the non-rough surface of the substrate. A light source from the side of the microscope side of the substrate was needed in order to assess whether or not the adhesive was in contact with the rough surface of the substrate.

The glass slides were placed in a climate controlled cabinet at 32° C. with a relative humidity of 20%.

The desired adhesive/paste to be investigated was circular with a 15 mm diameter and a thickness of 1 mm. The adhesive/paste was placed in a climate-controlled chamber with a temperature of 32° C. and a relative humidity of 20%. The sample was equilibrated to these conditions.

A load of 100 g with a flat contact surface of 15 mm in diameter was also placed in the climate-controlled chamber until the temperature of this was also 32° C.

After equilibrating the adhesive/paste and the load these were assembled so that the adhesive was mounted on the contact surface of the load.

The sample adhesive/paste, which was now mounted to the load, was placed on to the rough surface of the substrate while observing via the image feed from the microscope. The microscope was placed at an appropriate distance to the sample and the magnification was adequate in order to observe the entire are of contact without having to move the sample or microscope in respect to one another.

After 30 seconds of contact, a picture was taken via the microscope image feed documenting the area covered by the adhesive.

The obtained images were analysed in order to be able to differentiate where the adhesive was in contact with the rough surface of the substrate and where it was not. This was done using a specially written program that analyses the colour of the individual pixels of the image and comparing these to two reference images. The first reference image was obtained when the adhesive/paste was first brought into contact with the rough substrate. The secondary reference image was obtained after applying sufficient pressure to make the adhesive/paste sample get 100% contact with the rough substrate. Utilizing this procedure, it was possible to quantify the area of contact between the adhesive/paste and the rough substrate.

EXAMPLES

As examples, different compositions were manufactured and the relevant parameters were measured. The making of the different composition is described herein below. The compositions are numbered as follows for easy reference:

| Composition | Description |
| --- | --- |
| 1 | BASF acResin A 260 UV, no added photoinitiator, no added hydrocolloids |
| 2 | BASF acResin A 260 UV with 1% photoinitiator |
| 3 | BASF acResin A 260 UV with 1% photoinitiator and 25% mixed hydrocolloids |
| 4 | BASF acResin A 260 UV with 25% mixed hydrocolloids |
| 5 | BASF acResin A 260 UV with 50% mixed hydrocolloids |
| 6 | Aroset 1450 Z 40 with 1% photoinitiator |
| 7 | Aroset 1450 Z 40 with 1% photoinitiator and 25% mixed hydrocolloids |

| Composition | Description |
|---|---|
| 8 | BASF acResin A 260 UV with 0.5% photoinitiator, 25% tackifier, and 25% mixed hydrocolloids |
| 9 | BASF acResin A 260 UV with 0.51% photoinitiator, 5.63% acrylate, 18.75% tackifier, and 25% mixed hydrocolloids |
| 10 | Photo-crosslinkable polyurethane with built-in photoinitiator, 10% tackifier, and 25% mixed hydrocolloids |
| 11 | Photo-crosslinkable polyurethane with built-in photoinitiator, 12% tackifier, and 10% mixed hydrocolloids |
| 12 | Mixed moisture-switchable silicone adhesive with 10% mixed hydrocolloids |
| 13 | Mixed moisture-switchable silicone adhesive with 10% potato starch |
| 14 | Mixed moisture-switchable silicone adhesive with 10% carboxymethylcellulose |
| 15 | Mixed moisture-switchable silicone adhesive with 10% dried mixed hydrocolloids |
| 16 | Mixed moisture-switchable silicone adhesive with 10% dried carboxymethylcellulose |
| 17 | Mixed moisture-switchable silicone adhesive with 40% mixed, dried hydrocolloids |
| 18 | Mixed moisture-switchable silicone adhesive with 20% mixed, dried hydrocolloids |

Whenever compositions 1-7 are used in the switched state, the switch is performed by a 30-second exposure to the light source at a distance of 10 cm from the adhesive sample. The used light Source is a 24-bulb LED with an intensity of UVV (395-445 nm)=31 mW/cm$^2$ after 10 seconds measured at a distance of 2 cm from the measuring UV Power Puck II & UVICURE plus II.

Whenever compositions 8 and 9 are used in a switched state, the switch is performed as follows. The switch is performed by 10 minutes exposure to the light source at a distance of 8 cm from the adhesive sample with a polyurethane film (PU 30 μm thickness, BIA WEL 1BU AD) in between the acrylic adhesive and the light source. The used light Source is a 24-bulb LED with an intensity of UVV (395-445 nm)=31 mW/cm$^2$ 20 after 10 seconds measured at a distance of 2 cm from the measuring UV Power Puck II & UVICURE plus II.

Whenever compositions 10 and 11 are used in a switched state, the switch is performed as follows. The composition is switched by exposure to light on a conveyor belt from a Light Hammer® 6 lamp with an H bulb in a filter box, which only allows light between 320-480 nm to go through. The speed of the conveyor belt was 0.5 m/min. The distance from the composition to the lamp was 15 cm. The lamp was used with 60% of the maximum power. With these settings, measurements by a MicroCure® 2 UVA radiometer from EIT Inc. showed that the irradiance was 285 mW/cm$^2$ and the dose was 2061 mJ/cm$^2$. Three passes under lamp was performed in order to reach the switched state.

Whenever compositions 12-18 are used in a switched state, the switch is performed by exposing the adhesive to moisture in a specified way for a specified time. For instance, the switch may be performed by storing the adhesive in a humidity cupboard at 50% humidity for 48 hours. Other humidity levels and switching times may be used.

Materials

Acrynax 4326 solid acrylic adhesive polymer (Franklin International)

Akucell AF 2881 carboxymethyl cellulose (CMC) (Akzo Nobel)

Aroset 1450 Z 40 (40% solvent) (acrylic based polymer from Ashland)

BASF acResin A 260 UV (acrylic ester based polymer from BASF, Composition 1)

BIO-PSA 7-4560 Silicone Adhesive (Dow Corning)

Gelatine UF 220 (PB Gelatins)

Guar gum FG-200 (Hercules Corp.)

Irgacure 784 photoinitiator from Ciba (Bis(.eta.5-2,4-cylcopentadien-1-yl)-bis(2,6-difluoro-3-(1H-pyrrol-1-yl)-phenyl) titanium)

Pectin LM 12 CG-Z (CP Kelco)

Potato starch

Sylvares TR A25L clear, liquid polyterpene tackifier resin (Arizona Chemical)

TI7012 solid resin tackifier (Dow Corning)

Toluene

Trio Silken moisture sensitive silicone polymer (Trio Healthcare)

BASF acResin A 260 UV-Based Compositions

These exemplary compositions use the acrylate BASF acResin A 260 as the polymer in the composition. A photoinitiator, namely Irgacure 784 from Ciba, is used as the switch initiator. Light activates the photoinitiator and thus causes the switch.

Composition 2: BASF acResin A 260 UV with 1% Photoinitiator 80 g BASF acResin A 260 UV was dissolved in 120 mL toluene at room temperature using a shaker with a speed of 30 rpm.

60 g of the resulting solution was mixed with 0.24 g Irgacure 784 photoinitiator using a spatula for 1 min.

Using the obtained mixture, films were coated on release liner. Coatings were kept at room temperature overnight to evaporate toluene. After evaporation of toluene, coatings of 200-150 μm were obtained and covered with polyethylene film. The samples were rested for 24 hours before testing.

Composition 3: BASF acResin A 260 UV with 1% Photoinitiator and 25% Hydrocolloids For the compositions that were to contain 25% hydrocolloids, 2 g of hydrocolloid mixture (10% (w/w) pectin LM CG, CP Kelco, 20% (w/w) Akucell AF288, Akzo Nobel, 30% (w/w) PB gelatine, PB Gelatins and 40% (w/w) Guar gum FG-20, Hercules Corp.) was added to 15 g of the mixture containing BASF acResin A 260 UV with 1% photoinitiator as described above.

Composition 4: BASF acResin A 260 UV with 25% Hydrocolloids

A 70 g Z blade mixer was preheated to 90° C. and 52.2 g BASF acResin A 260 UV was put in to the mixer. This was mixed under vacuum for 10 min at 33 rpm. 17.5 g of the Hydrocolloid mixture (10% (w/w) pectin LM CG, CP Kelco, 20% (w/w) Akucell AF288, Akzo Nobel, 30% (w/w) PB gelatine, PB Gelatins and 40% (w/w) Guar gum FG-20, Hercules Corp.) was added to the mixer and mixed for 10 min without vacuum and 35 min with vacuum. The resulting composition was heat pressed to the required thickness between 2 siliconized papers in a heat press at 90° C. for 30 sec. The pressed composition rested for 24 hours before testing.

Composition 5: BASF acResin A 260 UV with 50% Hydrocolloids

A 70 g Z blade mixer was preheated to 90° C. and 35 g BASF acResin A 260 UV was put in to the mixer. This was mixed under vacuum for 10 min at 33 rpm. 35 g of the hydrocolloid mixture (10% (w/w) pectin LM CG, CP Kelco, 20% (w/w) Akucell AF288, Akzo Nobel, 30% (w/w) PB gelatine, PB Gelatins and 40% (w/w) Guar gum FG-20, Hercules Corp.) was added to the mixer and mixed for 5 min without vacuum and 20 min with vacuum. The resulting composition was heat pressed to the required thickness between 2 siliconized papers in a heat press at 90° C. for 30 sec. The pressed composition rested for 24 hours before testing.

Aroset 1450 Z 40 Based Compositions

These exemplary compositions use the commercially available acrylate Aroset 1450 Z 40 (40% solvent) as the polymer in the composition. A photoinitiator, namely Irgacure 784 from Ciba, is used as the switch initiator.

Composition 6: Aroset 1450 Z 40 Based Composition with 1% Photoinitiator 60 g of the Aroset 1450 Z 40 solution was mixed with 0.24 g Irgacure 784 photoinitiator using a spatula for 1 min.

Using the mixture, films were coated on release liner. Coatings were kept at room temperature overnight to evaporate toluene. After evaporation of toluene, films samples of 100-150 µm were obtained and covered with polyethylene film. The samples were rested for 24 hours before testing.

Composition 7: Aroset 1450 Z 40 Based Composition with 1% Photoinitiator and 25% Hydrocolloids For the compositions that were to contain 25% hydrocolloids, 2 g of hydrocolloid mixture (10% (w/w) pectin LM CG, CP Kelco, 20% (w/w) Akucell AF288, Akzo Nobel, 30% (w/w) PB gelatine, PB Gelatins and 40% (w/w) Guar gum FG-20, Hercules Corp.) was added to 15 g of the mixture containing Aroset 1450 Z 40 compound, toluene and photoinitiator, and mixed for 1 min using a spatula.

Tackified BASF acResin A 260 UV-Based Compositions

For these compositions, the hydrocolloid mixture was used as mixture of the above-mentioned particles: 10% (w/w) pectin, 20% (w/w) CMC, 30% (w/w) gelatine, and 40% (w/w) guar gum.

The compositions were prepared using a 60 g capacity Brabender blade mixer at 90° C. with 30 rpm (rotations per minute Composition 8: BASF acResin A 260 UV with 0.5% Photoinitiator, 25% Tackifier, and 25% Mixed Hydrocolloids 29.7 g of acResin BASF A 260 UV were mixed with 15 g of Sylvares TR A25L for 3 minutes. Afterwards, 15 g of hydrocolloids mixture and 0.30 g Irgacure 784 were added to the mixture and let mix for 20 minutes.

Composition 9: BASF acResin A 260 UV with 0.51% Photoinitiator, 5.63% Acrylate, 18.75% Tackifier, and 25% Mixed Hydrocolloids 30.07 g of acResin BASF A 260 UV were mixed with 3.38 g of Acrynax 4326 and with 11.25 g of Sylvares TR A25L for 3 minutes. Afterwards, 15 g of hydrocolloids mixture and 0.30 g Irgacure 784 were added to the mixture and let mix for 20 minutes.

Photoreactive Polyurethane Compositions

The photo-crosslinkable polyurethane was prepared in the laboratory according to the procedure below.

A 2000 mL 3-necked flask was charged with hydroxy terminated poly(dimethylsiloxane), PDMS diol (Aldrich product no. 481246; 508.1 g; Mn~5600 Da) and purged with nitrogen. The thioxanthone diol (11.0 g) solution in dry tetrahydrofuran, THF (850 mL) was added. The mixture was stirred at 65° C. under a gentle stream of nitrogen until a near homogeneous bright yellow solution was obtained. 4,4'-Methylenebis(cyclohexyl isocyanate), HMDI (32.1 g) was charged to the mixture followed by dibutyltin dilaurate (2.5 mL). Immediate exothermic reaction is observed and the reaction mixture started to reflux. The homogeneous reaction mixture was heated under reflux (68° C.) under nitrogen for 7 hours and then allowed to cool to ambient temperature overnight under a gentle stream of nitrogen. The reaction was then restarted and warmed to 70° C. for further 2 hours. The warm viscous reaction mass was partially evaporated until ca 300 mL THF remained in the crude product. At this stage, water (100 mL) was charged into the flask and agitation was continued for 1 hour at 70° C. to ensure complete hydrolysis of any residual isocyanate. The remaining solvent and water were then evaporated and the highly viscous yellow-orange residue was dried under oil pump vacuum for 2 hours. This provided the photo-crosslinkable polyurethane as a bright yellow/orange gummy semisolid in near quantitative yield.

Composition 10: Photo-Crosslinkable Polyurethane with 10% Tackifier and 25% Mixed Hydrocolloids 84.5 g Photo-crosslinkable polyurethane and 13.0 g TI7012 were dissolved in 84 g ethyl acetate using a magnetic stirrer at room temperature for 23 hours. 32.5 g (dry weight) of the hydrocolloid mixture (20% (w/w) Akucell AF 2881, 30% (w/w) Gelatine UF 220, 40% (w/w) Guar Gum FG-200, 10% (w/w) Pectin LM 12 CG-Z/200 was added to the ethyl acetate solution and stirred for 15 minutes. Subsequently, the mixture was coated on polyurethane film (A) or release liner (B).

(A) The coatings on the polyurethane film were made by using an applicator, which resulted in a thickness of 1000 µm before drying. The coatings were kept at 25° C. for 2 days to evaporate ethyl acetate. After evaporation of ethyl acetate, the coatings were approximately 400 µm.

(B) An applicator of 750 µm was used to prepare the coating on release liner. The coatings were kept at 25° C. for 2 days to evaporate ethyl acetate. After evaporation of ethyl acetate, the coatings were folded four to five times. The folded coating material was pressed between two release liners in a heat press at 90° C. for 5 seconds to obtain a thickness of 1 mm. The pressed composition rested overnight before testing.

Composition 11: Photo-Crosslinkable Polyurethane with 12% Tackifier and 10% Mixed Hydrocolloids 101.4 g Photo-crosslinkable polyurethane and 15.6 g TI7012 were dissolved in 101.4 g ethyl acetate using a magnetic stirrer at room temperature for 23 hours. 13.0 g (dry weight) of the hydrocolloid mixture (20% (w/w) Akucell AF 2881, 30% (w/w) Gelatine UF 220, 40% (w/w) Guar Gum FG-200, 10% (w/w) Pectin LM 12 CG-Z/200 was added to the ethyl acetate solution and stirred for 15 minutes. Subsequently, the mixture was coated on polyurethane film (A) or release liner (B).

(A) The coatings on the polyurethane film were made by using an applicator, which resulted in a thickness of 1000 µm before drying. The coatings were kept at 25° C. for 2 days to evaporate ethyl acetate. After evaporation of ethyl acetate, the coatings were approximately 400 µm.

(B) An applicator of 750 µm was used to prepare the coating on release liner. The coatings were kept at 25° C. for 2 days to evaporate ethyl acetate. After evaporation of ethyl acetate, the coatings were folded four to five times. The folded coating material was pressed between two release liners in a heat press at 90° C. for 5 seconds to obtain a thickness of 1 mm. The pressed composition rested overnight before testing.

Moisture Switchable Compositions

Composition 12: Mixed Moisture-Switchable Silicone Adhesive with 10% Mixed Hydrocolloids Trio Silken (18 g, 36 wt %, Trio Healthcare) was mixed with a mixture of hydrocolloids (5 g, 10 wt %) using Speedmixer at 3000 rpm for 3 minutes. The hydrocolloid mixture consists of carboxymethyl cellulose (20 wt %), guar gum (40 wt %), gelatin (30 wt %) and pectin (10 wt %). An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a polyurethane Biatin film (30 µm) using an applicator. For the switch experiments, this composition was switched in either an oven at 32° C., or in a humidity cupboard (Binder KBF) at 32° C. and 50% relative humidity.

Composition 13: Mixed Moisture-Switchable Silicone Adhesive with 10% Potato Starch Trio Silken (18 g, 36 wt %, Trio Healthcare) was mixed with a mixture of potato starch (5 g, 10 wt %) using Speedmixer at 3000 rpm for 3 minutes. An unreactive silicone polymer, BioPSA (27 g, 54 wt %, Dow Corning 7-4560), was added to the mixture, and the mixture was mixed using Speedmixer for additional 3 minutes at 3000 rpm. The resulting mixture was coated on a PU Biatin film using an applicator. For the switch experiments, this composition was switched in an oven at 32° C.

Composition 14: Mixed Moisture-Switchable Silicone Adhesive with 10% Carboxymethylcellulose Trio Silken (18 g, 36 wt %, Trio Healthcare) was mixed with a mixture of carboxymethylcellulose (5 g, 10 wt %) using Speedmixer at 3000 rpm for 3 minutes. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a PU Biatin film (30 µm) using an applicator. For the switch experiments, this composition was switched in an oven at 32° C.

Composition 15: Mixed Moisture-Switchable Silicone Adhesive with 10% Dried Mixed Hydrocolloids Trio Silken (18 g, 36 wt %, Trio Healthcare) was mixed with a mixture of hydrocolloids (5 g, 10 wt %) using Speedmixer at 3000 rpm for 3 minutes. The hydrocolloid mixture consists of carboxymethyl cellulose (20 wt %), guar gum (40 wt %), gelatin (30 wt %) and pectin (10 wt %). Hydrocolloids were dried prior to use in an oven at 80° C. The total moisture content of the hydrocolloids were measured as 2.28 wt %. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a polyurethane Biatin film (30 µm) using an applicator. For the switch experiments, this composition was switched in an oven at 32° C.

Composition 16: Mixed Moisture-Switchable Silicone Adhesive with 10% Dried Carboxymethylcellulose Trio Silken (18 g, 36 wt %, Trio Healthcare) was mixed with dried CMC (5 g, 10 wt %) using Speedmixer at 3000 rpm for 3 minutes. Hydrocolloids were dried prior to use in an oven at 80° C. The total moisture content of the hydrocolloids were measured as 2.73 wt %. An unreactive silicone polymer, BioPSA (27 g, 54 wt %, Dow Corning 7-4560) was added to the mixture, and the mixture was mixed using Speedmixer for additional 3 minutes at 3000 rpm. The resulting mixture was coated on a PU Biatin film (30 µm) using an applicator. For the switch experiments, this composition was switched in an oven at 32° C.

Composition 17: Mixed Moisture-Switchable Silicone Adhesive with 40% Dried Mixed Hydrocolloids Trio Silken (12 g, 24 wt %, Trio Healthcare) was mixed with a mixture of hydrocolloids (20 g, 40 wt %) using Speedmixer at 3000 rpm for 3 minutes. The hydrocolloid mixture consists of carboxymethyl cellulose (20 wt %, Akucell AF 2881, Akzo Nobel), guar gum (40 wt %, guar gum FG-200, Nordisk Gelatine), gelatin (30 wt %, gelatin UF220, PB Gelatins GmbH) and pectin (10 wt %, LM 12 CG-Z/200, CP Kelco). The hydrocolloids were dried at 80° C. before being added to the formulation until they reached a water content of 2.43 wt %. An unreactive silicone polymer, BioPSA (18 g, 36 wt %, Dow Corning 7-4560) was added to the mixture, and the mixture was mixed using Speedmixer for additional 3 minutes at 3000 rpm. The resulting mixture was coated on a film using an applicator, and the film was cured in an oven at 32° C. with a relative humidity of 50% before testing.

Composition 18: Mixed Moisture-Switchable Silicone Adhesive with 40% Dried Mixed Hydrocolloids Trio Silken (15 g, 30 wt %, Trio Healthcare) was mixed with a mixture of hydrocolloids (10 g, 50 wt %) using Speedmixer at 3000 rpm for 3 minutes. The hydrocolloid mixture consists of carboxymethyl cellulose (20 wt %, Akucell AF 2881, Akzo Nobel), guar gum (40 wt %, guar gum FG-200, Nordisk Gelatine), gelatin (30 wt %, gelatin UF220, PB Gelatins GmbH) and pectin (10 wt %, LM 12 CG-Z/200, CP Kelco). The hydrocolloids were dried at 80° C. before being added to the formulation until they reached a water content of 2.16 wt %. An unreactive silicone polymer, BioPSA (22.5 g, 45 wt %, Dow Corning 7-4560) was added to the mixture, and the mixture was mixed using Speedmixer for additional 3 minutes at 3000 rpm. The resulting mixture was coated on a film using an applicator, and the film was cured in an oven at 32° C. with a relative humidity of 50% before testing.

Results

A summary of all the results is presented in the below table A1, A2, and A3. All the individual measurements and results are further described and discussed in the following sections.

TABLE A1

| | Comp. # | | | | | |
|---|---|---|---|---|---|---|
| | 1 | 2 | 3 | 4 | 5 | 6 |
| Type | Acrylate | Acrylate | Acrylate | Acrylate | Acrylate | Acrylate |
| Switch | Light | Light | Light | Light | Light | Light |
| Hydrocolloids | None | None | 25% | 25% | 50% | None |
| First peel[1] N/25 mm | | 6.20 | 3.76 | | | 1.41 |
| Repeated peel[2] | | 6.44 | 3.21 | | | 2.08 |
| Viscosity[3] Pa s, 0.01 Hz | 25,883 | (25,883) | (76,562) | 76,563 | 169,307 | |
| Wetting[4] | 96% | | | 80% | 61% | |
| Abs.[5] (g/cm²/2 h) | | | 0.12 | 0.14 | 0.25 | |
| Swelling[6] mm | | | 3.5 | 4.5 | 5 | |

[1]Measured after switch on substrate.
[2]Measured after switch on substrate, detachment, and re-attachment.
[3]Viscosity measured before switch. Values in parenthesis are estimated.
[4]Wetting measured prior to switch.
[5]Absorption of switched adhesive composition.
[6]Swelling value measured by the erosion test of the switched adhesive composition.

TABLE A2

| | Comp. # | | | | | |
|---|---|---|---|---|---|---|
| | 7 | 8 | 9 | 10 | 11 | 12[7] |
| Type | Acrylate | Acrylate | Acrylate | PU | PU | Silicone |
| Switch | Light | Light | Light | Light | Light | Moisture |
| Hydrocolloids | 25% | 25% | 25% | 25% | 10% | 10% |
| First peel[1] N/25 mm | 1.54 | 12.34 | 8.92 | 2.08 | 1.30 | 3.04 |
| Repeated peel[2] | 1.02 | 8.44 | 6.95 | 1.23 | 1.50 | 3.02 |
| Viscosity[3] Pa s, 0.01 Hz | | 10,890 | 16,790 | 87,970 | 47,740 | 351 |
| Wetting[4] | | 72% | 46% | 18% | 51% | 72% |
| Abs.[5] (g/cm²/2 h) | | 0.07 | 0.07 | 0.02 | 0.01 | 0.01 |
| Swelling[6] mm | | 0.8 | 0.3 | 0,5 | 0 | 0 |

[1]Measured after switch on substrate.
[2]Measured after switch on substrate, detachment, and re-attachment.
[3]Viscosity measured before switch. Values in parenthesis are estimated.
[4]Wetting measured prior to switch.
[5]Absorption of switched adhesive composition.
[6]Swelling value measured by the erosion test of the switched adhesive composition.
[7]Oven-cured sample.

TABLE A3

| | Comp. # | | | | | |
|---|---|---|---|---|---|---|
| | 13 | 14 | 15 | 16 | 17 | 18 |
| Type | Silicone | Silicone | Silicone | Silicone | Silicone | Silicone |
| Switch | Moisture | Moisture | Moisture | Moisture | Moisture | Moisture |
| Hydrocolloids | 10% | 10% | 10% | 10% | 40% | 20% |
| First peel[1] N/25 mm | 3.39 | 2.44 | 1.14 | 1.03 | 1.47 | 1.86 |
| Repeated peel[2] | 3.10 | 2.04 | 1.26 | 1.01 | 1.16 | 1.52 |
| Viscosity[3] Pa s, 0.01 Hz | 310 | 328 | 1,072 | 1,557 | 2,366 | 795 |

TABLE A3-continued

| | Comp. # | | | | | |
|---|---|---|---|---|---|---|
| | 13 | 14 | 15 | 16 | 17 | 18 |
| Wetting[4] | 82% | 90% | | | | |
| Absorption[5] (g/cm²/2 h) | 0.01 | 0.01 | | | 0.03 | 0.01 |
| Swelling[6] mm | 0 | 0 | | | | |

[1]Measured after switch on substrate.
[2]Measured after switch on substrate, detachment, and re-attachment.
[3]Viscosity measured before switch. Values in parenthesis are estimated.
[4]Wetting measured prior to switch.
[5]Absorption of switched adhesive composition.
[6]Swelling value measured by the erosion test of the switched adhesive composition.

MVTR

TABLE 1a

MVTR results, compositions 2, 3, 6, and 7

| Sample | Thickness (μm) | Adhesive + film MVTR (g/m²/24 h) |
|---|---|---|
| BL9601 film reference | 17 | 11,600 |
| Composition 2, switched | 115 | 290 |
| Composition 3, switched | 155 | 1,150 |
| Composition 6, switched | 105 | 370 |
| Composition 7, switched | 145 | 2,020 |

Table 1a demonstrates that the adhesive compositions 3 and 7 with hydrocolloids are much more moisture vapor permeable than compositions 2 and 6, which do not contain hydrocolloids.

TABLE 1b

MVTR results, compositions 8 and 9

| Sample | Thickness (μm) | Adhesive + film MVTR (g/m²/24 h) |
|---|---|---|
| BL9601 film reference | 30 | 5,292 |
| Composition 8, non-switched | 400 | 1,268 |
| Composition 8, switched | 400 | 2,151 |
| Composition 9, non-switched | 410 | 1,166 |
| Composition 9, switched | 410 | 2,364 |

TABLE 1c

MVTR results, compositions 10 and 11

| Sample | Thickness (μm) | Adhesive + Film MVTR (g/m2/24 h) |
|---|---|---|
| Composition 10, not switched | 400 | 4,362 |
| Composition 10, switched | 400 | 900 |
| Composition 11, not switched | 400 | 470 |
| Composition 11, switched | 400 | 468 |

TABLE 1d

MVTR results, compositions 12, 13, and 14

| Sample | Thickness (μm) | Adhesive + Film MVTR (g/m2/24 h) |
|---|---|---|
| Film used in Composition 12-14 | 30 | Not applicable |
| Composition 12 (oven), 48 h switch time | 336 | 439 |
| Composition 12 (humidity cupboard), 48 h switch time | 343 | 500 |
| Composition 13 (oven), 48 h switch time | 382 | 499 |
| Composition 14 (oven), 48 h switch time | 531 | 572 |

As seen in Table 1d, for these moisture switch compositions, the MVTR values are fairly low and do not vary much between the compositions.

Erosion

TABLE 2a

Erosion results, compositions 3, 4, and 5

| Sample | Thickness (μm) | Eroded away? | Swelling (mm) |
|---|---|---|---|
| Composition 3, not switched | 500 | No | 5 |
| Composition 3, switched | 500 | No | 3.5 |
| Composition 4 | 500 | No | 4.5 |
| Composition 5 | 500 | No | 5 |

In general, a very good resistance to erosion is seen. With higher filling rate, meaning a larger proportion of filler materials, such as hydrocolloids, in the composition, a larger swelling is seen. The switched sample has a better resistance to water after 24 h as it has characteristics more like a pressure sensitive adhesive than a liquid.

TABLE 2b

Erosion results, compositions 8 and 9

| Sample | Thickness (μm) | Eroded away? | Swelling (mm) |
|---|---|---|---|
| Composition 8, not switched | 400 | No | 2.0 |
| Composition 8, switched | 400 | No | 0.8 |
| Composition 9, not switched | 400 | Yes | 8.0 |
| Composition 9, switched | 400 | No | 0.3 |

Only the non-switched Composition 9 eroded away. As expected, the non-switched samples show a higher swelling and erosion due to the lower cross-linking.

TABLE 2c

Erosion results, compositions 10 and 11

| Sample | Thickness (μm) | Eroded away? | Swelling (mm) |
|---|---|---|---|
| Composition 10, not switched | 390 | Yes | 7 |
| Composition 10, switched | 385 | No | 0.5 |
| Composition 11, not switched | 395 | No | 0 |
| Composition 11, switched | 408 | No | 0 |

As seen in table 2c, significant erosion was seen in the non-switched composition 10. Almost no erosion is seen in composition 10 after switch, demonstrating the stability of the switched compositions. No erosion was seen in composition 11.

TABLE 2d

Erosion results, compositions 12, 13, and 14

| Sample | Thickness (μm) | Eroded away? | Swelling (mm) |
|---|---|---|---|
| Composition 12 (oven), 48 h switch time | 336 | No | 0 |
| Composition 12 (humidity cupboard), 48 h switch time | 376 | No | 0 |
| Composition 13 (oven), 48 h switch time | 356 | No | 0 |
| Composition 14 (oven), 48 h switch time | 440 | No | 0 |

No erosion was seen in these moisture switchable compositions.

Moisture Absorption

TABLE 3a

Moisture absorption results, compositions 3, 4, and 5

| Sample | Adhesive thickness (μm) | Moisture absorption (g/cm$^2$/2 h) |
|---|---|---|
| Composition 3, not switched | 500 | 0.15 |
| Composition 3, switched | 500 | 0.12 |
| Composition 4 | 500 | 0.14 |
| Composition 5 | 500 | 0.25 |

As expected, the moisture absorption capacity increases with an increasing content of hydrocolloids. There was no difference in the absorption as a consequence of adding the photoinitiator to the adhesive composition. Only a slight decrease in moisture absorption was observed when going from the non-switched to the switched state of the BASF acResin A 260 UV mixture with 25% hydrocolloids.

TABLE 3b

Moisture absorption results, compositions 8 and 9

| Sample | Adhesive thickness (μm) | Moisture absorption (g/cm$^2$/2 h) |
|---|---|---|
| Composition 8, not switched | 400 | 0.15 |
| Composition 8, switched | 400 | 0.07 |
| Composition 9, not switched | 400 | 0.14 |
| Composition 9, switched | 400 | 0.06 |

The non-switched composition are doubling the water absorption capacities, comparing to the switched ones. There is only a small difference in the moisture absorption capacities between the two compositions. This could be due to the same quantity of the hydrocolloids added to the composition.

TABLE 3c

Moisture absorption results, compositions 10 and 11

| Sample | Adhesive thickness (μm) | Moisture absorption (g/cm$^2$/2 h) |
|---|---|---|
| Composition 10, not switched | 415 | 0.06 |
| Composition 10, switched | 415 | 0.02 |
| Composition 11, not switched | 415 | 0.01 |
| Composition 11, switched | 415 | 0.01 |

As expected, Composition 10, which contains 25% hydrocolloids, displayed a higher moisture absorption than composition 11, which only contains 10% hydrocolloids.

TABLE 3d

Moisture absorption results, compositions 12, 13, and 14

| Sample | Adhesive thickness (μm) | Moisture absorption (g/cm$^2$/2 h) |
|---|---|---|
| Composition 12 (oven), 48 h switch time | 365 | 0.01 |
| Composition 12 (humidity cupboard), 48 h switch time | 475 | 0.01 |
| Composition 13 (oven), 48 h switch time | 440 | 0.01 |
| Composition 14 (oven), 48 h switch time | 450 | 0.01 |

As expected, these compositions with 10% hydrocolloids displayed only modest moisture absorption.

TABLE 3e

Moisture absorption results, compositions 17 and 18

| Sample | Adhesive thickness (μm) | Moisture absorption (g/cm$^2$/time) | | | |
|---|---|---|---|---|---|
| | | 5 min | 30 min | 2 h | 24 h |
| Composition 17 (oven), 48 h switch time | 400 | 0.02 | 0.03 | 0.03 | 0.06 |
| Composition 17, not switched | 400 | 0.02 | 0.04 | 0.08 | 0.25 |

TABLE 3e-continued

Moisture absorption results, compositions 17 and 18

| Sample | Adhesive thickness (μm) | Moisture absorption (g/cm²/time) | | | |
|---|---|---|---|---|---|
| | | 5 min | 30 min | 2 h | 24 h |
| Composition 18 (oven), 48 h switch time | 400 | 0.01 | 0.01 | 0.01 | 0.03 |

As expected, these composition with a higher hydrocolloid content displayed high moisture absorption. Composition 17 contains 40% hydrocolloids and composition 18 contains 20% hydrocolloids. The higher hydrocolloid content in composition 17 leads to both higher initial and long-term absorption. Just for comparison, the absorption values for the non-switched composition 17 are also indicated. These are considerably higher than for the switched composition, which may reflect, inter alia, the lower cohesion of the switched composition.

Peel

Samples were either attached to a substrate and peeled without having been switched at all ("non-switched"), attached to the substrate, then switched, and then peeled ("1$^{st}$ peel"), or attached to a substrate, then switched, then peeled, and then re-attached and peeled a second time ("2$^{nd}$ repeated peel", may also be referred to simply as "second peel" or "repeated peel").

TABLE 4a

Peel results, compositions 2, 3, 6, and 7

| Sample | Non-switched (N/25 mm) | 1$^{st}$ peel (N/25 mm) | 2$^{nd}$ repeated peel (N/25 mm) |
|---|---|---|---|
| Composition 2 | CF * | 6.20 | 6.44 |
| Composition 3 | CF * | 3.76 | 3.21 |
| Composition 6 | 3.40 | 1.41 | 2.08 |
| Composition 7 | 3.24 | 1.54 | 1.02 |

* Cohesive failure while performing the peel test of the non-switched samples

Generally, the BASF acResin A 260 UV failed cohesively in the non-switched state. This was expected due to the low viscosity of these compositions. Cohesive failure means that the adhesives cannot be pulled off the substrate in one piece but rather comes apart cohesively and leaves substantial residue on the substrate. Cohesive failure generally means that the cohesive forces holding the adhesive together are weaker than the adhesive forces holding the adhesive and the substrate together.

For the hydrocolloid-containing compositions, there was a tendency towards a somewhat lower second repeated peel force as compared to the first peel force. However, for all samples the repeated peel force was above 1 N/25 mm, which illustrates the ability of the compositions to exhibit PSA-like behaviour in the switched adhesive state. In particular, the value of the repeated peel force demonstrates that these switched compositions act by adherence to the substrate rather than solely by mechanical anchoring established in the non-switched state.

TABLE 4b

Peel results, compositions 8 and 9

| Sample | Non-switched (N/25 mm) | 1$^{st}$ peel (N/25 mm) | 2$^{nd}$ (N/25 mm) |
|---|---|---|---|
| Composition 8 | CF * | 12.34 | 8.44 |
| Composition 9 | CF * | 8.92 | 6.95 |

* Cohesive failure while performing the peel test of the non-switched samples

From the results above it can be seen that very high peel forces values from Teflon substrate can be achieved by using these compositions. The non-switched samples are breaking cohesively.

The switched samples are peeling with very high peel forces from the Teflon substrate (>8 N/25 mm).

The second repeated peel values are over 5 N/25 mm in both cases, suggesting a very high ability of the acrylic based material to re-bond with the substrate after having once been peeled off. This clearly demonstrates the pressure sensitive adhesive character of the switched composition.

TABLE 4c

Peel results, compositions 10 and 11

| Sample | Non-switched (N/25 mm) | 1$^{st}$ peel (N/25 mm) | 2$^{nd}$ repeated peel (N/25 mm) |
|---|---|---|---|
| Composition 10 | 1.26 | 2.08 | 1.23 |
| Composition 11 | 1.60 | 1.30 | 1.50 |

Both compositions 10 and 11 displayed significantly high repeated peel values above 1 N/25 mm.

TABLE 4d

Peel results, compositions 12, 13, and 14

| Sample | Non-switched (N/25 mm) | 1$^{st}$ peel (N/25 mm) | 2$^{nd}$ repeated peel (N/25 mm) |
|---|---|---|---|
| Composition 12 (oven) 48 h switch time | CF * | 3.04 | 3.02 |
| Composition 12 (humidity cupboard) 48 h switch time | CF * | 2.24 | 3.70 |
| Composition 13 (oven) 48 h switch time | CF * | 3.39 | 3.10 |
| Composition 14 (oven) 48 h switch time | CF * | 2.44 | 2.04 |
| Composition 15 (oven) 48 h switch time | CF * | 1.14 | 1.26 |
| Composition 16 (oven) 48 h switch time | CF * | 1.03 | 1.01 |
| Composition 17 (oven) 48 h switch time | CF * | 1.47 | 1.16 |
| Composition 18 (oven) 48 h switch time | CF * | 1.86 | 1.52 |

* Cohesive failure for all compositions in the first liquid state.

Moisture switching adhesives are materials, which switch from sticky liquid state to less sticky solid state when in contact with moisture. Storage stability, particularly in the sense of avoiding switching during storage, and switching speed of moisture switching formulations are two important parameters for their use in ostomy care. These formulations contain an unreactive, hydrophobic and sticky polymer to provide adhesion to skin, a reactive and hydrophobic polymer for switching, and hydrophilic particles for absorbing body fluids from the skin.

Since the switching reaction takes place upon exposing the materials to moisture or water, the amount of water/moisture introduced by adding hydrophilic particles is a very important parameter, which will determine the storage stability and switching speed. A possible issue with regard to storage stability is the reaction of water in hydrophilic particles with the reactive groups in the hydrophobic polymer, which will lead to switching of the formulation during storage. We hypothesize that this unwanted issue can be prevented by adding hydrophilic particles with the suitable content of water to find the right balance between storage stability and switching speed during use. To support this hypothesis, we made formulations using hydrophilic particles with different levels of water, and show that formulations made of hydrophilic particles with less water switches faster, evidenced by measurements of peel force and viscosity. Measurements of peel force provide an indirect measure of switching, while viscosity is a direct measure of switching. As switching progresses, the peel force is expected to decrease, whereas viscosity is expected to increase. Our results prove that adjusting the water levels in hydrophilic particles is a handle to tune the storage stability and switch speed. In particular, compare the peel and viscosity measurements for compositions 12 (non-dried mix of hydrocolloids) and 15 (same composition, but with dried mix of hydrocolloids), and compositions 14 (non-dried CMC) and 16 (dried CMC).

Complex Viscosity $|\eta^*|$ and Wetting

The complex viscosity was measured in exemplary compositions as described herein. Also, a set of wetting experiments were carried out as described herein. The results are displayed below.

For practical reasons, the measurements on compositions 1-5 were carried out without addition of photoinitiator. The presence of a small amount, e.g. 1%, of photoinitiator would not be expected to significantly change the properties of the compositions in terms of viscosity and wetting. This means that, at least in terms of the viscosities, the values obtained for compositions 1 and 4 will be the values we would expect also for compositions 2 and 3, respectively.

TABLE 5a

Complex viscosity $|\eta^*|$ and wetting results, compositions 1, 4, and 5

| Sample | $|\eta^*|$ at frequency 0.01 Hz (Pa s) | Wetting at 100 g and 30 seconds |
| --- | --- | --- |
| Composition 1 | 25,883 | 96% |
| Composition 4 | 76,563 | 80% |
| Composition 5 | 169,307 | 61% |

From Table 5 it can be seen that for compositions with a relatively low complex viscosity a high degree of wetting is seen—whereas for higher viscosities a lower degree of wetting is seen. These results indicate that by decreasing the complex viscosity of a composition it is possible to increase the ability of a system to wet a rough substrate.

During the above experiments, it was seen that the amount of hydrocolloid mixed into the system had an impact on the complex viscosity and also the degree of wetting seen within the measured time frame. It can also be seen that the compositions tested all exhibit a relatively low complex viscosity and also a relatively high degree of wetting—all above 60%. These results indicate that having a composition containing hydrocolloids does not necessarily fully impair the composition to flow into and wet a rough substrate.

TABLE 5b

Complex viscosity $|\eta^*|$ and wetting results, compositions 8 and 9

| Sample | $|\eta^*|$ at frequency 0.01 Hz (Pa s) | Wetting at 100 g and 30 seconds |
| --- | --- | --- |
| Composition 8 | 10,890 | 72% |
| Composition 9 | 16,790 | 46% |

The complex viscosity ($|\eta^*|$) of these compositions are well under 20,000 Pa s, with a well-defined low-viscous paste-like behaviour. Each of the components added to the compositions is having its own impact on the final complex viscosity value, e.g., Acrynax in a 10% concentration determines an increase of $|\eta^*|$ comparing to Composition 8.

TABLE 5c

Complex viscosity $|\eta^*|$ and wetting results, compositions 10 and 11

| Sample | $|\eta^*|$ at frequency 0.01 Hz (Pa s) | Wetting at 100 g and 30 seconds |
| --- | --- | --- |
| Composition 10, not switched (E4A) | 87,970 | 18% |
| Composition 11, not switched (E5A) | 47,740 | 51% |

The relatively high viscosity of composition 10 is matched by a quite low wetting value. In contrast, composition 11 displayed much lower viscosity and also the expected higher wetting, thereby again confirming the relationship between viscosity and wetting.

TABLE 5d

Complex viscosity $|\eta^*|$ and wetting results, compositions 12, 13, and 14

| Sample | $|\eta^*|$ at frequency 0.01 Hz (Pa s) | Wetting at 100 g and 30 seconds |
| --- | --- | --- |
| Composition 12, not switched | 351 | 72% |
| Composition 12, switched, 48 h switch time | 8,020 | |
| Composition 13, not switched | 310 | 82% |
| Composition 14, not switched | 328 | 90% |
| Composition 15, not switched | 1,072 | |
| Composition 15, switched, 48 h switch time | 163,000 | |
| Composition 16, not switched | 1,557 | |
| Composition 16, switched, 48 h switch time | 95,500 | |
| Composition 17, not switched | 2,366 | |
| Composition 18, not switched | 795 | |

The viscosity measurements of the switched compositions clearly illustrate the shift to a higher viscosity following the switch. For practical reasons, these post-switch viscosities were measured by using the following DMA settings: Frequency sweep at a deformation of 1% and 2N normal force, sample thickness of 400 um, and test temperature is 32° C.

The invention claimed is:

1. A switchable adhesive composition comprising a polymer, a photo-crosslinkable polyurethane, and a hydrocolloid, wherein the switchable adhesive composition can be switched from a liquid state to an adhesive state by activation of the photo-crosslinkable polyurethane; the switchable adhesive composition having in the liquid state a complex viscosity |η*| below 0.4 MPa s; and having in the adhesive state a higher complex viscosity |η*| than the complex viscosity |η*| of the liquid state, and having in the adhesive state a repeated peel force above 1 N/25 mm.

2. The switchable adhesive composition according to claim 1, wherein the switchable adhesive composition in the adhesive state has a first peel force above 1 N/25 mm.

3. The switchable adhesive composition according to claim 1, wherein the switchable adhesive composition in the adhesive state has a first peel force and wherein the repeated peel force is at least 50% of the first initial peel force.

4. The switchable adhesive composition according to claim 1, wherein the polymer is an acrylate polymer or an acrylate copolymer.

5. The switchable adhesive composition according to claim 4, wherein the acrylate polymer or acrylate copolymer comprises monomer units selected from ethyl acrylate, butyl acrylate, ethylhexyl acrylate, hydroxyethyl acrylate, lauryl acrylate, and acrylic acid.

6. The switchable adhesive composition according to claim 1, wherein the polymer is a polyurethane.

7. The switchable adhesive composition according to claim 6, wherein the polyurethane comprises a diisocyante selected from the group consisting of cycloaliphatic isocyanates, 4,4'-Methylenebis(cyclohexyl isocyanate) (HMDI), isophore diisocyanate, aromatic isocyanates, tolylene diisocyanate, 4,4'-diphenyl methyl diisocyanate (MDI), aliphatic isocyanates, and 1,6-hexane diisocyanate.

8. The switchable adhesive composition according to claim 6, wherein the polyurethane comprises a diol of polydimethylsiloxane (PDMS) based polyols, bis(hydroxyalkyl) terminated PDMS, 4-{3-[bis(2-hydroxyethyl)amino]propoxy}-1-chloro-9H-thioxanthen-9-one (thioxanthone diol) and mixtures thereof.

9. The switchable adhesive composition according to claim 1, wherein the photo-crosslinkable polyurethane comprises a free radical generating photoinitiator.

10. The switchable adhesive composition according to claim 1, wherein the photo-crosslinkable polyurethane includes a photoinitiator moiety comprising an α-hydroxyketone, a benzophenone, benzophenone derivatives, a benzophenone/α-hydroxyketone, phenylglyoxylate, a benzyldimethyl-ketal, an aminoketone, acylphosphine derivatives, mono acyl phosphine (MAPO), MAPO/α-hydroxyketone, bis acyl phosphine (BAPO), a BAPO dispersion, a BAPO/α-hydroxyketone, phosphine oxide, a metallocene, an ionium salt, thioxanthone derivatives, a mixture of triarylsulphonium hexafluorophosphate salts in propylene carbonate, a mixture of triarylsulphonium hexafluoroantimonate salts in propylene carbonate, amphorquinone derivatives, benzil derivatives, anthraquinone derivatives, benzoin ether derivatives, polysilanes, and mixtures thereof.

11. The switchable adhesive composition according to claim 1, wherein the activation of the photo-crosslinkable polyurethane is caused by exposure of the photo-crosslinkable polyurethane to visible light and/or ultraviolet light.

12. The switchable adhesive composition according to claim 1, wherein the switchable adhesive composition comprises the hydrocolloid in an amount of 1-60% (w/w) of the switchable adhesive composition.

13. The switchable adhesive composition according to claim 1, wherein the hydrocolloid is a guar gum, a locust bean gum, a pectin, a potato starch, alginates, a gelatine, a xantan, a gum karaya, cellulose derivatives, salts of carboxymethyl cellulose, a sodium carboxymethyl cellulose, a methyl cellulose, a hydroxypropyl cellulose, a hydroxyethyl cellulose, a sodium starch glycolate, polyvinylalcohol, and mixtures thereof.

14. The switchable adhesive composition according to claim 1, wherein the switchable adhesive composition in the liquid state has moisture absorption of at least 0.1 g/cm³/2 h.

15. The switchable adhesive composition according to claim 1, wherein the switchable adhesive composition in the adhesive state has moisture absorption of at least 0.05 g/cm³/2 h.

16. The switchable adhesive composition according to claim 1, wherein the moisture absorption of the switchable adhesive composition in the liquid state is higher than the absorption of the moisture in the adhesive state.

17. The switchable adhesive composition according to claim 1, wherein the switchable adhesive composition in the liquid state and/or the adhesive state is moisture vapor permeable.

18. The switchable adhesive composition according to claim 1, wherein the moisture vapor transmission rate (MVTR) of the switchable adhesive composition in the liquid state is above 250 g/m²/24 h.

19. The switchable adhesive composition according to claim 1, wherein the moisture vapor transmission rate (MVTR) of the switchable adhesive composition in the adhesive state is above 250 g/m²/24 h.

20. The switchable adhesive composition according to claim 1, wherein the switchable adhesive composition in the adhesive state has a G' in the range $10^3$-$10^5$ Pa at 1 Hz.

21. The switchable adhesive composition according to claim 1, wherein the switchable adhesive composition in the adhesive state has a G'' in the range $10^3$-$10^5$ Pa at 1 Hz.

22. The switchable adhesive composition according to claim 1, wherein the switchable adhesive composition in the liquid state has a complex viscosity |η*| below 0.1 MPa s.

23. The switchable adhesive composition according to claim 1, wherein the switchable adhesive composition in the adhesive state has a complex viscosity that is at least 2 times higher than the complex viscosity of the switchable adhesive composition in the liquid state.

24. The switchable adhesive composition according to claim 1, wherein the switchable adhesive composition in the liquid state has a lower cohesion than the switchable adhesive composition in the adhesive state.

25. The switchable adhesive composition according to claim 1, wherein the switchable adhesive composition is hydrophobic.

26. The switchable adhesive composition according to claim 1, wherein the switchable adhesive composition is hydrophilic.

27. The switchable adhesive composition according to claim 1, wherein the polymer forms a hydrophobic polymer matrix.

28. The switchable adhesive composition according to claim 1, wherein the switchable adhesive composition is a one-component switchable adhesive composition.

29. The switchable adhesive composition according to claim 1, wherein the complex viscosity |η*| is measured on 1 mm thick 25 mm diameter sample in a Haake RheoStress 6000 rotational rheometer, wherein the geometry applied was parallel plates 25 mm, the shear stress was fixed at 5556 Pa, and a gap size of 0.9-1.05 mm was applied to the sample in the beginning of the measurement to obtain a normal force of approximately 5 N, and wherein the measurements were carried out at 32° C. and at a frequency of 0.01 Hz.

30. The switchable adhesive composition according to claim 1, wherein the repeated peel force is measured on a sample of 25×100 mm with a 25×300 mm piece of tape added on the top of the switchable adhesive composition, wherein the measurement is carried out after 30 minutes of conditioning at 23° C. and at 50% relative humidity with the sample mounted in a tensile testing machine (INSTRON 5564) and a 90-degree peel test performed from a Teflon substrate at a speed of 304 mm/min.

31. A re-attachable ostomy device comprising:
   an ostomy device having a switchable adhesive composition disposed thereon,
   wherein the switchable adhesive composition comprises a polymer, a photo-crosslinkable polyurethane, and a hydrocolloid, wherein the switchable adhesive composition can be switched from a liquid state to an adhesive state by activation of the photo-crosslinkable polyurethane; the switchable adhesive composition having in the liquid state a complex viscosity $|\eta^*|$ below 0.4 MPa s; and
having in the adhesive state a higher complex viscosity $|\eta^*|$ than the complex viscosity $|\eta^*|$ of the liquid state, and having in the adhesive state a repeated peel force above 1 N/25 mm.

* * * * *

UNITED STATES PATENT AND TRADEMARK OFFICE
CERTIFICATE OF CORRECTION

PATENT NO. : 11,045,576 B2
APPLICATION NO. : 15/517519
DATED : June 29, 2021
INVENTOR(S) : Lam et al.

It is certified that error appears in the above-identified patent and that said Letters Patent is hereby corrected as shown below:

In the Specification

In Column 2, Lines 59-60, delete "diisocyante" and insert -- diisocyanate --, therefor.

In Column 2, Line 62, delete "isophore diisocyanate," and insert -- isophorone diisocyanate, --, therefor.

In Column 2, Line 63, delete "tolylene" and insert -- toluene --, therefor.

In Column 3, Line 14, delete "mono acyl phosphine" and insert -- mono(acyl)phosphine oxide --, therefor.

In Column 3, Line 15, delete "bis acyl phosphine" and insert -- bis(acyl)phosphine oxide --, therefor.

In Column 3, Line 27, delete "tricarbonylchronium," and insert -- tricarbonylchromium, --, therefor.

In Column 3, Line 28, delete "cyclopentadienyliron(II)hexafluorophophate," and insert -- cyclopentadienyliron(II)hexafluorophosphate, --, therefor.

In Column 6, Line 48, delete "second," and insert -- seconds, --, therefor.

In Column 7, Line 9, delete "On Ostomy" and insert -- An Ostomy --, therefor.

In Column 9, Line 23, delete "where" and insert -- were --, therefor.

In Column 14, Line 27, delete "19 second" and insert -- 19 seconds --, therefor.

In Column 17, Line 1, delete "diisocyante" and insert -- diisocyanate --, therefor.

In Column 17, Line 3, delete "diisocyante" and insert -- diisocyanate --, therefor.

Signed and Sealed this
Fifth Day of April, 2022

Drew Hirshfeld
*Performing the Functions and Duties of the*
*Under Secretary of Commerce for Intellectual Property and*
*Director of the United States Patent and Trademark Office*

In Column 17, Line 60, delete "isophore diisocyanate," and insert -- isophorone diisocyanate, --, therefor.

In Column 17, Line 61, delete "tolylene" and insert -- toluene --, therefor.

In Column 18, Line 29, delete "thioxanthene diol" and insert -- thioxanthone diol --, therefor.

In Column 22, Line 22, delete "mono acyl phosphine" and insert -- mono(acyl)phosphine oxide --, therefor.

In Column 22, Line 23, delete "bis acyl phosphine" and insert -- bis(acyl)phosphine oxide --, therefor.

In Column 22, Lines 33-34, delete "tricarbonylchronium," and insert -- tricarbonylchromium, --, therefor.

In Column 22, Lines 34-35, delete "cyclopentadienyliron(II)hexafluorophophate," and insert -- cyclopentadienyliron(II)hexafluorophosphate, --, therefor.

In Column 22, Line 47, delete "erythhrosin B)," and insert -- erythrosin B), --, therefor.

In Column 28, Line 31, delete "are of" and insert -- area of --, therefor.

In Column 33, Line 30, delete "Biatin" and insert -- Biatain --, therefor.

In Column 33, Line 42, delete "Biatin" and insert -- Biatain --, therefor.

In Column 33, Line 53, delete "Biatin" and insert -- Biatain --, therefor.

In Column 34, Line 2, delete "Biatin" and insert -- Biatain --, therefor.

In Column 34, Line 16, delete "Biatin" and insert -- Biatain --, therefor.

In Columns 35 and 36, In Table A2, Line 14, delete "0,5" and insert -- 0.5 --, therefor.

In the Claims

In Column 45, Line 28, in Claim 7, delete "diisocyante" and insert -- diisocyanate --, therefor.

In Column 45, Line 31, in Claim 7, delete "isophore diisocyanate," and insert -- isophorone diisocyanate, --, therefor.

In Column 45, Line 31, in Claim 7, delete "tolylene" and insert -- toluene --, therefor.

In Column 45, Line 49, in Claim 10, delete "mono acyl phosphine" and insert -- mono(acyl)phosphine oxide --, therefor.

In Column 45, Line 50, in Claim 10, delete "bis acyl phosphine" and insert -- bis(acyl)phosphine oxide --, therefor.